(12) United States Patent
Tuli

(10) Patent No.: US 12,310,751 B2
(45) Date of Patent: May 27, 2025

(54) PROCESS FOR MANUFACTURING AN MONITORING SYSTEM

(71) Applicant: Raja Singh Tuli, Montreal (CA)

(72) Inventor: Raja Singh Tuli, Montreal (CA)

(*) Notice: Subject to any disclaimer, the term of this patent is extended or adjusted under 35 U.S.C. 154(b) by 900 days.

(21) Appl. No.: 17/186,397

(22) Filed: Feb. 26, 2021

(65) Prior Publication Data

US 2021/0282710 A1    Sep. 16, 2021

Related U.S. Application Data

(60) Provisional application No. 62/988,669, filed on Mar. 12, 2020.

(51) Int. Cl.
| | |
|---|---|
| *A61B 5/00* | (2006.01) |
| *A61F 13/15* | (2006.01) |
| *A61F 13/42* | (2006.01) |
| *A61F 13/53* | (2006.01) |

(52) U.S. Cl.
CPC .......... *A61B 5/6808* (2013.01); *A61B 5/0004* (2013.01); *A61B 5/0015* (2013.01); *A61F 13/15577* (2013.01); *A61F 13/53* (2013.01); *A61F 2013/15121* (2013.01); *A61F 2013/15715* (2013.01); *A61F 2013/424* (2013.01); *A61F 2013/53089* (2013.01)

(58) Field of Classification Search
CPC ........ A61B 2562/029; A61B 2562/046; A61B 2562/12; A61B 5/0004; A61B 5/0015; A61B 5/207; A61B 5/6808; A61F 13/15577
See application file for complete search history.

(56) References Cited

U.S. PATENT DOCUMENTS

| | | | | |
|---|---|---|---|---|
| 6,774,800 | B2* | 8/2004 | Friedman | A61F 13/42 340/573.5 |
| 7,394,391 | B2* | 7/2008 | Long | A61F 13/42 340/573.5 |
| 9,498,394 | B2* | 11/2016 | Hu | A61F 13/15699 |
| 2005/0252968 | A1* | 11/2005 | Tsujimura | G06K 17/0025 400/76 |
| 2019/0167490 | A1* | 6/2019 | Hellmold | G01N 27/126 |
| 2021/0282710 | A1* | 9/2021 | Tuli | A61B 5/207 |

* cited by examiner

*Primary Examiner* — Minh N Trinh

(57) ABSTRACT

A process for manufacturing an excretion monitoring system is provided that comprises: providing, on a liquid-impervious material roll, a plurality of radio frequency (RF) tags in an arrangement each of the plurality of RF tags is configured to respond to a signal at a different frequency; repeating, along length of the liquid-impervious material roll and throughout the entire length of the liquid-impervious material roll, the providing the plurality of RF tags; cutting in a manner nondeterministic to the RF tags the liquid-impervious material roll into sections of a predetermined length such that there contains approximately the plurality of RF tags in each section; and constituting the excretion monitoring system by using one of the sections. Contact of a RF tag with an excreted fluid modifies a response by that RF tag to a signal at the corresponding frequency.

6 Claims, 18 Drawing Sheets

PROCESS FOR MANUFACTURING AN MONITORING SYSTEM

CROSS-REFERENCE TO RELATED APPLICATIONS

This application claims priority to U.S. provisional patent application No. 62/988,669, entitled "REMOTE INCONTINENCE DETECTION AND MONITORING SYSTEM WITH METHOD AND MANUFACTURING METHOD THEREOF," filed on Mar. 12, 2020. The content of this application is hereby incorporated by reference in its entirety for all purposes.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable

STATEMENT REGARDING PRIOR DISCLOSURES BY THE INVENTOR OR A JOINT INVENTOR

Not Applicable

BACKGROUND OF THE INVENTION

Field of the Invention

The present invention relates to a system to remotely detect and monitor incontinence in a diaper-like product with no need for a pod to establish electrical connection between wet sensors.

Description of the Related Art

With the growing age of the population there is an increased need of adult protection against incontinence like diapers, pads or briefs to name a few. For the purpose of clarity this description will refer to diapers but other incontinence protections are within the scope of this disclosure.

Institutions like hospitals and retirement homes face the challenge of providing care to residents. Such care includes timely changing the resident's diapers, in order to prevent several problems ranging from health issue and patients' comfort, to diapers consumption and laundry management.

One course of action came in the form of diapers including sensors. Those sensors come in different forms of strips. They can be incorporated in the diaper during the diaper manufacturing or by modifying the diaper after. They can also be added to the diaper for instance in the form of sensor strips.

The existing art significantly relies on pods that are clipped or attached to the diaper by various means and which purpose is to relay what the sensors detect to an external unit that will monitor the presence of liquid in the diaper and trigger the alarm for changing it. Some prior art diaper also includes components like electronic chips so the diaper monitors itself and will send a warning to change it.

As for the means to detect and monitor the presence of liquid in the diaper, the prior art mostly relies on the creation of an electric circuit formed by the combination of the sensors, the pod and the liquid released in the diaper. Detection and monitoring range from simply triggering an alarm when the diaper is wet, to triggering the alarm only when the diaper reaches its saturation level.

One shortcoming of electrical circuits formed by the combination of sensors and pods is that variations in the electrical signals be caused by the manufacturing of the sensors or by the way the pods are installed. Indeed, if the pod is not properly installed and connected, the detection and monitoring might not be as efficient as expected. It also requires some training for caregiver to guarantee the sensors and pods are properly installed.

Another prior art wetness detection system is disclosed in US2004/0070510A1, in which a resonant tag is affixed to the diaper whose substantially constant resonant frequency is eliminated when its inductor is contacted by urine and in which a remote detection means emits a substantially constant swept frequency and activates an alarm when the resonant frequency is eliminated. A problem with this type of prior art wetness detection is that it requires a pre-manufactured resonant tag to be affixed to the diaper, which complicates the manufacture of the diaper with such wetness detection system. And with a resonant tag affixed to the diaper, such system can only determine whether the specific location of the resonant tag is contacted by urine, but cannot determine the saturation of the diaper.

Also, another prior art patient incontinence monitoring apparatus and method are disclosed in U.S. Pat. No. 6,774,800, in which a RF tag is positioned in contact with or in spaced relation with the liquid absorbent material and is configured to absorb a wireless excitation signal whereupon a change in the amount of discharged fluid received in the liquid absorbent material causes a change in the absorption of the energy of the wireless excitation signal by the RF tag. This prior art also requires a pre-manufactured resonant tag to be affixed to the diaper, which complicates the manufacture of the diaper with tag.

Thus, it is desirable to provide alternate means to detect and monitor incontinence without resorting to altering the diaper or significantly modifying its manufacturing process. It is desirable to offer a diaper that does not require the manual installation of sensors. It is desirable to offer a diaper that allows the detection and monitoring of incontinence without the need for a pod to relay the data detected by the sensor to the actual monitoring system. It is also desirable to offer a means to detect and monitor incontinence with precision and that is not subject to undesired variations and that does not require to resort to sophisticated components. It is also desirable to provide a cost-effective means to manufacture such a diaper which implies to displace the actual detection and monitoring process out of the diaper.

SUMMARY OF THE INVENTION

In an aspect, the present disclosure relates to a combination of a diaper with an external monitoring system. During the manufacturing of the diaper, rolls of materials are used and the diapers are cut at a pre-set length and the other features are added to finalize the product. Markers/tags are (pre-)printed on the material, and along the length of the diaper, in order to maintain a pre-set number of said markers/tags for each diaper. All manufactured diapers have the same number of markers/tags printed inside.

Each marker/tag is (pre-)printed to react to a determined individual radio frequency and the total number of markers printed in a diaper will always correspond to a pre-determined set of frequencies that will be repeated for every set of markers. Each manufactured diaper contains the same number of markers responding to the same set of pre-determined frequencies. As a result, a series of manufactured diaper will be identical when it comes to the number of markers and the frequencies they correspond to.

An external monitoring system comprises a transmitter and a receiver to send and receive a series of electromagnetic signals corresponding to the pre-set frequencies associated with the markers. As long as a marker is not exposed to a liquid, the signal transmitted from the transmitter at its frequency will be responded by the marker, e.g. be relayed or reflected by the marker towards the receiver or will be absorbed or interfered with by the marker so as not to be received by the receiver. When a marker is finally exposed to the liquid, its ability to relay or reflect or absorb or interfere with the signal is lost and the frequency associated to that particular marker becomes silent or appears at the receiver. As more and more liquid expands into the diaper, and said diaper gets saturated, more markers lose their ability to react to their frequency. Based on the absence or presence of the frequencies at the receiver and their emplacement it becomes possible to determine the moment the diaper has to be changed and alert the caregiver accordingly.

DETAILED DESCRIPTION OF THE PREFERRED EMBODIMENTS

Figure 1:
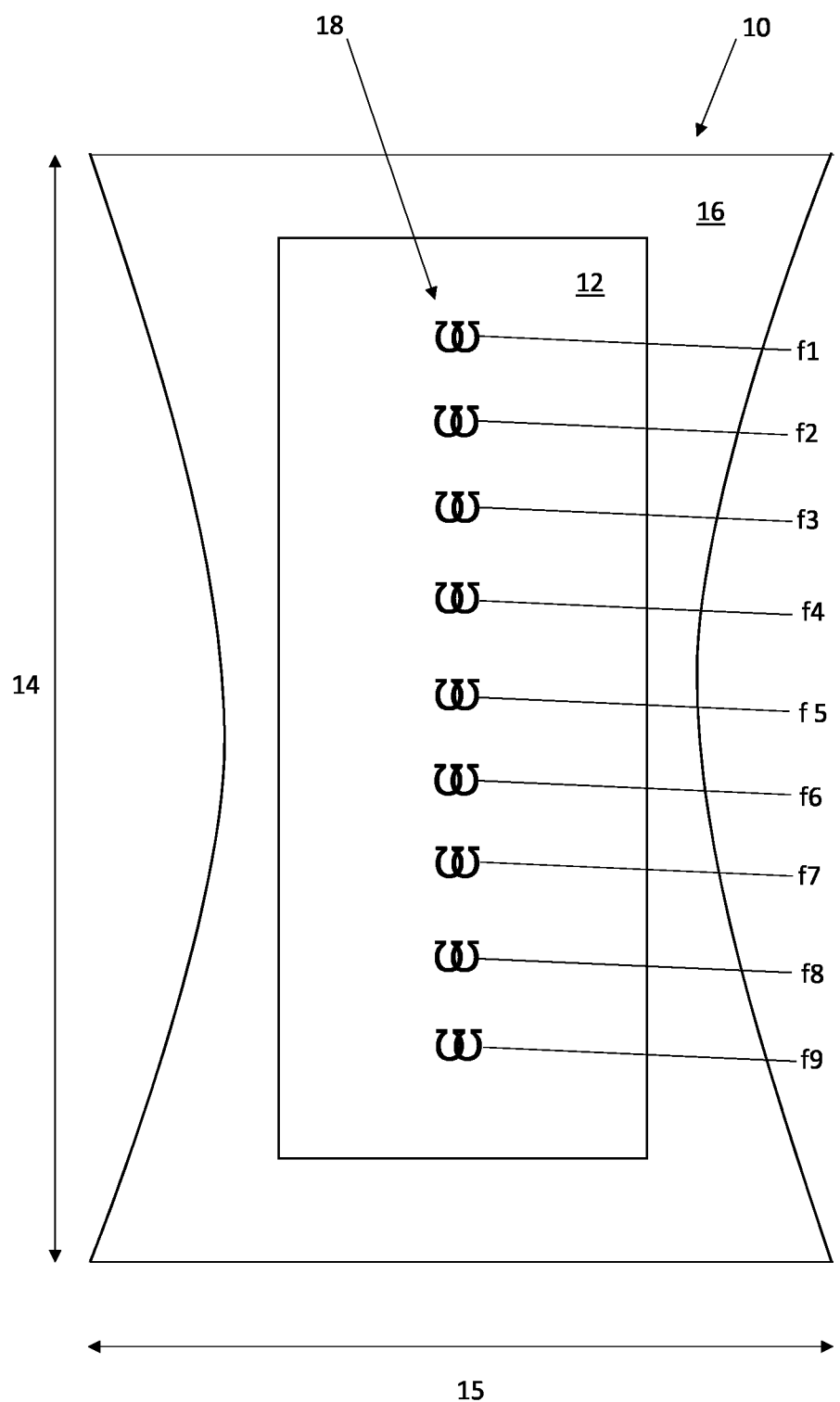
FIG. 1 is a schematic top view of an exemplary diaper according to an embodiment of the present disclosure.

FIG. 1 illustrates an exemplary diaper 10 with a length 14 and a width 15 according to an embodiment of the present disclosure. As appreciated by those skilled in the art, the diaper 10 is primarily composed of at least two layers of material: an absorbent layer 12 whose purpose is to absorb urine or any other body fluids and a liquid-impervious layer 16. It is appreciated that other constructions for diaper are possible and shall be considered to be within the scope of the present disclosure.

In the embodiments of the present disclosure, a plurality of tags 18 are provided on the liquid-impervious layer 16. Preferably, the tags 18 are provided on the inner side of the liquid-impervious layer 16 (i.e. the side facing the absorbent layer 12) with the absorbent layer 12 being situated on top of said tags 18, that is, the tags 18 are sandwiched between the inner side of the liquid-impervious layer 16, where they are provided, and the bottom side of the absorbent layer 12. And it is also possible to provide the tags on the outer side of the liquid-impervious layer 16 (i.e. the side opposite to the absorbent layer 12). In the illustrative embodiment as depicted in FIG. 1, nine tags 18 are provided on the central axis of diaper 10 along its length 14 on the inner side of the liquid-impervious layer 16 as an example. It is to be noted that the number (e.g. nine) and the arrangement (e.g. the centered disposition on the inner side of the liquid-impervious layer, the spacings) of the tags 18 as illustrated in FIG. 1 are for illustrative purpose only, and on the liquid-impervious layer 16 there may exist a different number of tags 18 being disposed in other arrangements, e.g. to the left or to the right, on the outer side, etc.

As illustrated in FIG. 1, each tag 18 is associated with a respective dedicated frequency. In particular, each tag 18 is provided or designed such that it operates with a respective dedicated frequency, that is, during normal operation each tag is operable to react to (e.g. resonate with and re-transmit, or relay, or reflect, or absorb, or interfere with, etc.) signal tuned to its respective dedicated frequency. As an example, in FIG. 1 from top to bottom, the nine tags 18 are associated with frequencies f1, f2, . . . , f9 respectively. In the embodiments of the present disclosure, the frequencies associated with the tags 18 are different from each other in a diaper, e.g. the frequencies f1, f2, . . . , f9 as illustrated in FIG. 1 are (slightly) different from each other.

Instead of first manufacturing the tags 18 and then inserting them in the diaper or on the liquid-impervious material/layer, the tags 18 are directly printed on the liquid-impervious material/layer 16 according to an embodiment of the present disclosure, in order to avoid the significant modification or complication in the diaper manufacturing assembly line.

As mentioned above, the tags 18 are provided or designed to operate with their respective dedicated frequencies. In an embodiment of the present disclosure, each tag 18 is configured to respond to a signal tuned to its respective dedicated frequency by being energized by that signal and then transmitting a signal at the same frequency back. For example, the tag 18 is configured to function as a LC resonant circuit with the resonant frequency being its respective dedicated frequency.

Figure 1A:
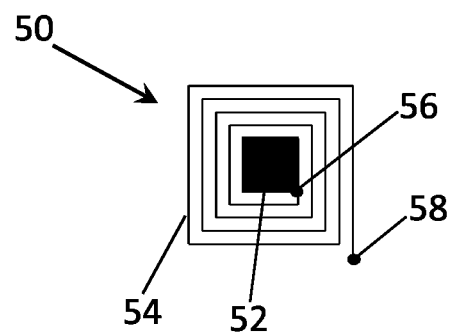
FIG. 1A illustrates a process for printing a RF tag with three layers, according to an embodiment of the present disclosure.
Figure 1A:
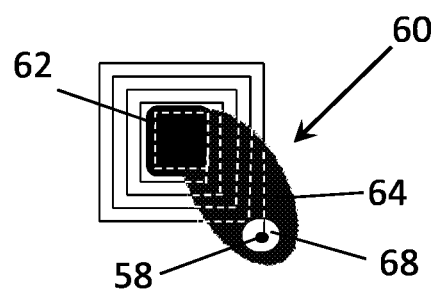
Figure 1A:
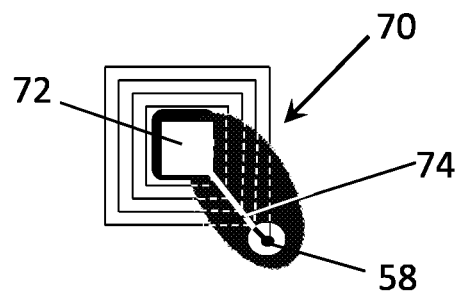

In an embodiment of the present disclosure where the tag 18 functions as a LC resonant circuit, the tag 18 can be provided by printing on the liquid-impervious material/layer a capacitor and an inductor, e.g. a center capacitor and an inductor arranged (e.g. as coil) around the capacitor. Please note that the capacitor and the inductor in a LC resonant tag can be arranged in another manner, which also can be used with the technical solutions of the present disclosure. As an example, the tag 18 is composed of three layers that are printed on the liquid-impervious material/layer, a first conductive layer 50, a second insulation layer 60, and a third conductive layer 70. FIG. 1A illustrates an exemplary process for printing a tag 18 according to an embodiment of the present disclosure.

As illustrated in the upper diagram of FIG. 1A, a first conductive layer 50 is printed on the liquid-impervious material/layer 16, in which a plate 52 is printed at center and a conductor 54 is printed spirally around the center plate 52 with its first terminal 56 being connected to the center plate 52. The conductor 54 also comprises a second terminal 58. It is appreciated that the conductor spirally around the center plate forms a coil, i.e. an inductor.

Next, a second insulation layer 60 is printed over the first conductive layer 50 in order to insulate the plate and the conductor in the first conductive layer 50 from those in the third conductive layer 70. In an embodiment of the present disclosure, the second insulation layer 60 covers at least the plate 52 and exposes at least the second terminal 58 and part of the conductor 54, e.g. the second insulation layer 60 only covers the center plate 52, and a connection portion from the center plate 52 to the second terminal 58, with a hole at the location of the second terminal 58 to expose it. For example, in the embodiment as illustrated in the middle diagram of FIG. 1A, the second insulation layer 60 is formed of a center insulation portion 62 that covers the center plate 52, and a connection insulation portion 64, with a hole 68 to expose the second terminal 58.

Then a third conductive layer 70 is printed on top of the second insulation layer 60 in which another plate 72 is formed at the location corresponding to the plate 52 (i.e. on the center insulation portion 62), and a conductor 74 is formed on the connection insulation portion 64 to connect the plate 72 with the exposed second terminal 58. It is appreciated that the two plates 52 and 72 separated by the center insulation portion 62 form a capacitor, the conductor 54 spirally around the plate 52 forms an inductor, and the capacitor and the inductor are connected by the conductor 74. It is also appreciated that by controlling e.g. the thickness of the center insulation portion 62 (i.e. the distance between the plates 52 and 72) and/of the area of the plates 52 and 72 and/or the number of turns of the coil formed by the conductor 54, a tag 18 can be printed with a desired resonant frequency, i.e. its dedicated frequency.

It will be appreciated that the three layers can be printed in an order opposite from that as illustrated in FIG. 1A. That is, first in the conductive first layer 50 that is printed on the liquid impervious layer the plate 72 and the conductor 74 are printed, next the second insulation layer 60 is printed over the first conductive layer 50, and then the third conductive layer 70 is printed on top of the second insulation layer in which the plate 52 and the conductor 54 (i.e. inductor) are printed.

In order to avoid the potential twist or bend, the tag 18 is made stiff in some embodiments of the present disclosure. For example, a stiffening layer such as e.g. a layer of polymer that is stiff can be added during the printing process of the tag 18 as illustrated in FIG. 1A. As a non-limiting example, during the printing process of a tag, a stiffening layer is first printed on the liquid-impervious layer/material, then the first conductive layer, the second insulation layer and the third conductive layer are printed on the stiffening layer as illustrated and described above. It is to be noted that the stiffening layer can be provided in another arrangement with respect to the other three layers, e.g. on the top of the three other layers, in particular on the top of the third conductive layer, or even between any two adjacent layers of the three other layers.

Alternatively, instead of adding an additional stiffening layer, at least one of the three layers (i.e. first conductive layer, the second insulation layer and the third conductive layer) of the tag is reinforced to be stiff, in some embodiments of the present disclosure. For example, at least one of the three layers is reinforced with some stiff polymer so as to be stiff. As another example, the second insulation layer can be simply made of some stiff polymer.

It is to be noted that the stiffening layer (either an additional stiffening layer or the one of the three layers (the first conductive layer, the second insulation layer and the third conductive layer) that is made stiff with stiff material) is configured to prevent the twist or bend of the tag as a whole, that is, the stiffening layer is configured to make the whole area or surface of the tag stiff. In order for that, the stiffening layer needs to cover the whole surface of the tag (e.g. in an embodiment where the stiffening layer is first printed on the liquid-impervious layer/material and then the first conductive layer, the second insulation layer and the third conductive layer are printed on the stiffening layer), or have several branches or sections to reach the external edges of the tag, e.g. in the star-like shape.

It is also to be noted that the stiffening layer is required to be provided in such a manner that does not interfere with the function and/or operation of the tag. In particular, after the addition of an additional stiffening layer or the construction of one of the three layers (the first conductive layer, the second insulation layer and the third conductive layer) as a stiffening layer, the tag 18 can still function as LC resonant circuit, and the contact of the excreted liquid such as the urine etc. with the tag 18 modifies the function and/or operation of the tag, e.g. modifies the response of the tag to the signal at the resonant frequency. For example, where the stiffening layer is provided above the third conductive layer, the stiffening layer is configured with some gaps or holes to allow the excreted liquid to go through to modify the function and/or operation of the tag.

In an embodiment, the tags 18 are printed on the liquid-impervious sheet, and the liquid-impervious sheet with the tags 18 is supplied in roll form and is conveyed into the diaper manufacturing assembly line to constitute the liquid-impervious layer 16 of the diaper to be manufactured. Alternatively, the tags 18 can be incorporated during the diaper manufacturing process with minimal modification to the manufacturing process, e.g. by including a printer or printers into the assembly line to print the tags 18 on (the inner or outer side of) the liquid-impervious material that is supplied without tags 18 being pre-printed thereon.

As appreciated by those skilled in the art, the liquid-impervious sheet for diaper production is provided in the form of large roll. In the embodiments of the present disclosure, in order to manufacture the diapers, the roll of the liquid-impervious sheet (regardless whether or not the tags 18 are already pre-printed thereon) is unrolled and the liquid-impervious sheet with tags 18 (either pre-printed or being printed by the printer(s) in the assembly line) is then combined with other layer(s) such as the absorbent layer 12 and is cut into sections of an appropriate size. Each said section contains the same set of tags in the same arrangement (i.e. the same number of tags, the same spacings and the same relative positions) and is used to form a single diaper. In an embodiment of the present disclosure, the tags 18 are printed on the liquid-impervious material/layer with a constant spacing between two consecutive adjacent tags, such that the same length of the sections can ensure the same number of tags being contained in each section.

Figure 2:
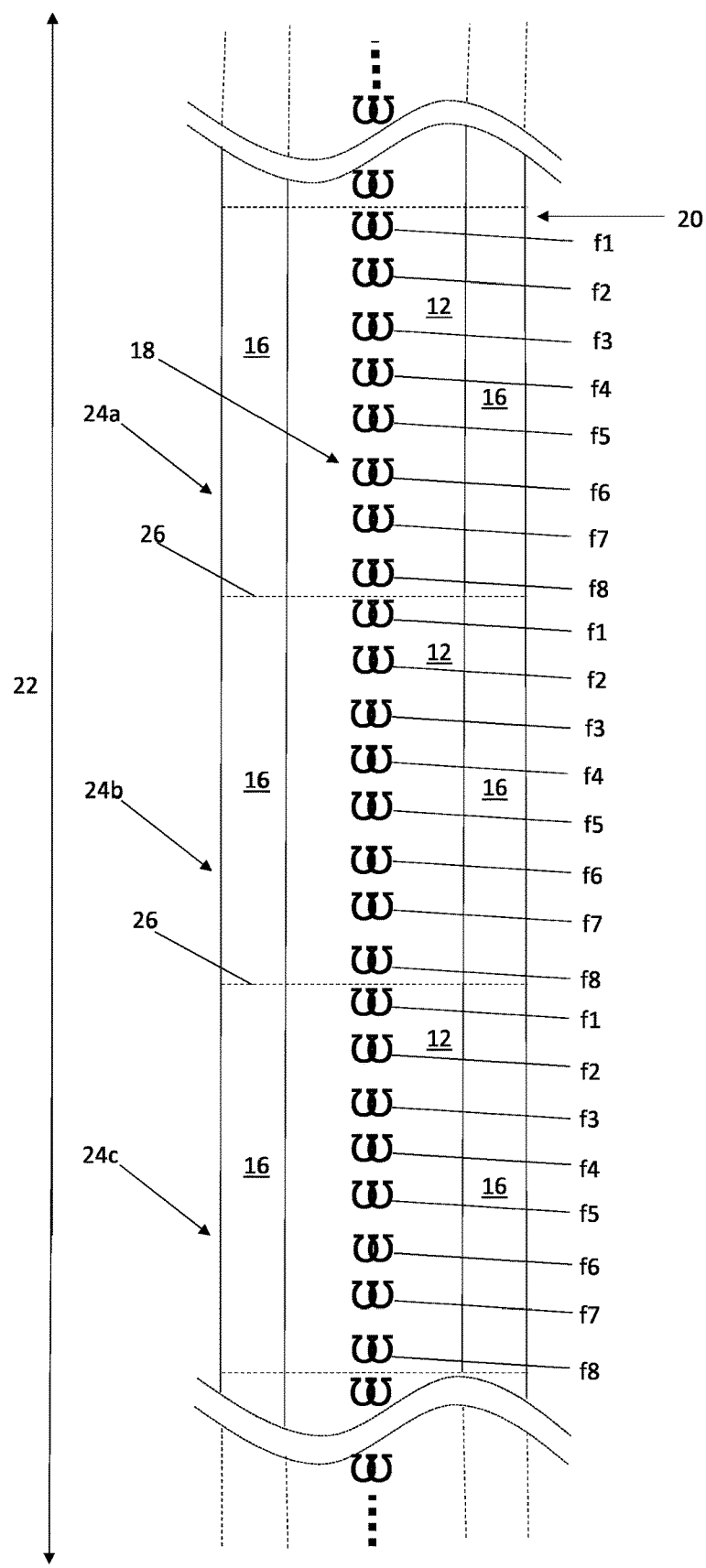
FIG. 2 is a schematic top view of an exemplary unrolled roll of material to manufacture diapers according to an embodiment of the present disclosure.

FIG. 2 illustrates an unrolled roll 20 of the liquid-impervious material/sheet with tags 18 on top of which the absorbent layer 12 is disposed, according to an embodiment of the present disclosure. As mentioned above, on the liquid-impervious sheet 20 the tags 18 either are pre-printed or are printed by the printer(s) in the assembly line. In the embodiments of the present disclosure, the tags 18 are pre-printed or printed in such a manner that a set of a pre-determined number of tags 18 is continuously repeated on the liquid-impervious sheet along its length with their arrangement (e.g. the spacings and relative positions) remaining unchanged, and that the tags 18 in one such set operate with different specific frequencies respectively. As an example, in the embodiment as depicted in FIG. 2 a set of eight tags 18 is continuously repeated in the same arrangement on the liquid-impervious sheet along its length, and the eight tags 18 in one such set operate with eight different frequencies f1, f2, . . . , f8 respectively. It is to be noted that the number and the arrangement of the tags 18 in one such set can be pre-determined as appropriate, e.g. based on the size of the diaper to be manufactured. In an embodiment of the present disclosure, the number of the tags 18 in one such set is pre-determined such that each manufactured diaper contains that number of tags 18 on the liquid impervious layer 16. Also, in order to facilitate the printing procedure of the tags on the liquid-impervious material/layer (either before or during the diaper manufacture process), the tags 18 in a such set is printed with descending/ascending frequencies, e.g. by gradually increasing/decreasing the thickness of the second insulation layer 60 and/or the area of the plates and/or the number of turns of the coils forming the inductors. As an example, in the embodiment as depicted in FIG. 2, f1>f2>f3>f4>f5>f6>f7>f8 or f1<f2<f3<f4<f5<f6<f7<f8.

As mentioned above, the liquid-impervious sheet 20, after combined with other layer(s) such as the absorbent layer 12, is cut into sections of an appropriate size, each of which contains the same set of a pre-determined number of tags in the same arrangement and is used to form a single diaper. In the embodiments of the present disclosure, the liquid-impervious sheet 20 together with the absorbent layer 12 among others is cut into sections such that in each section there contain the pre-determined number of the tags 18 as described above. As an example, the liquid-impervious sheet 20 together with the absorbent layer 12 is cut into sections 24 at the lines 26 such that a set of eight tags 18 is contained in each section 24, in the illustrative embodiment as depicted in FIG. 2. In FIG. 2, the line 26 is disposed between the tag 18 associated with the frequency f8 and the tag 18 associated with the frequency f1 as an example, that is, the eight tags 18 in each section 24 are respectively associated with eight different frequencies, f1, f2, f3, f4, f5, f6, f7, f8 sequentially from top to bottom.

It is to be noted that in the embodiments of the present disclosure it is not necessary to perform the cut operations at a specific location (e.g. always between two specific consecutive adjacent markers). Instead, the cut operations only need to be performed in such a manner that ensures the predetermined number of tags are contained in each section, e.g. the cut operations may be performed with a constant interval so as to obtain the sections with a constant length, which in turn leads to the same number of tags being contained in each section when the tags are printed with a constant spacing. It is appreciated that the disposition of the line 26 (i.e. the cut position) as illustrated in FIG. 2 is for illustrative purpose only, and shall not be construed as limiting the scope of this disclosure. Any other possible arrangement or disposition is considered to be within the scope of this disclosure. In the embodiments of the present disclosure, since a set of a predetermined number of tags 18 is repeated continuously on the liquid-impervious sheet 20, the cut can be repeatedly performed between any two sequential (adjacent) tags 18 to obtain the sections with the predetermined number of tags 18 being contained in each section. For example, in the embodiment as illustrated in FIG. 2, the liquid-impervious sheet 20 together with the absorbent layer 12 can be cut between the tag 18 associated with the frequency f3 and that associated with the frequency f4, such that in each section there contain eight tags 18 that are respectively associated with the eight different frequencies, f4, f5, f6, f7, f8, f1, f2, f3 sequentially from top to bottom.

Figure 3:
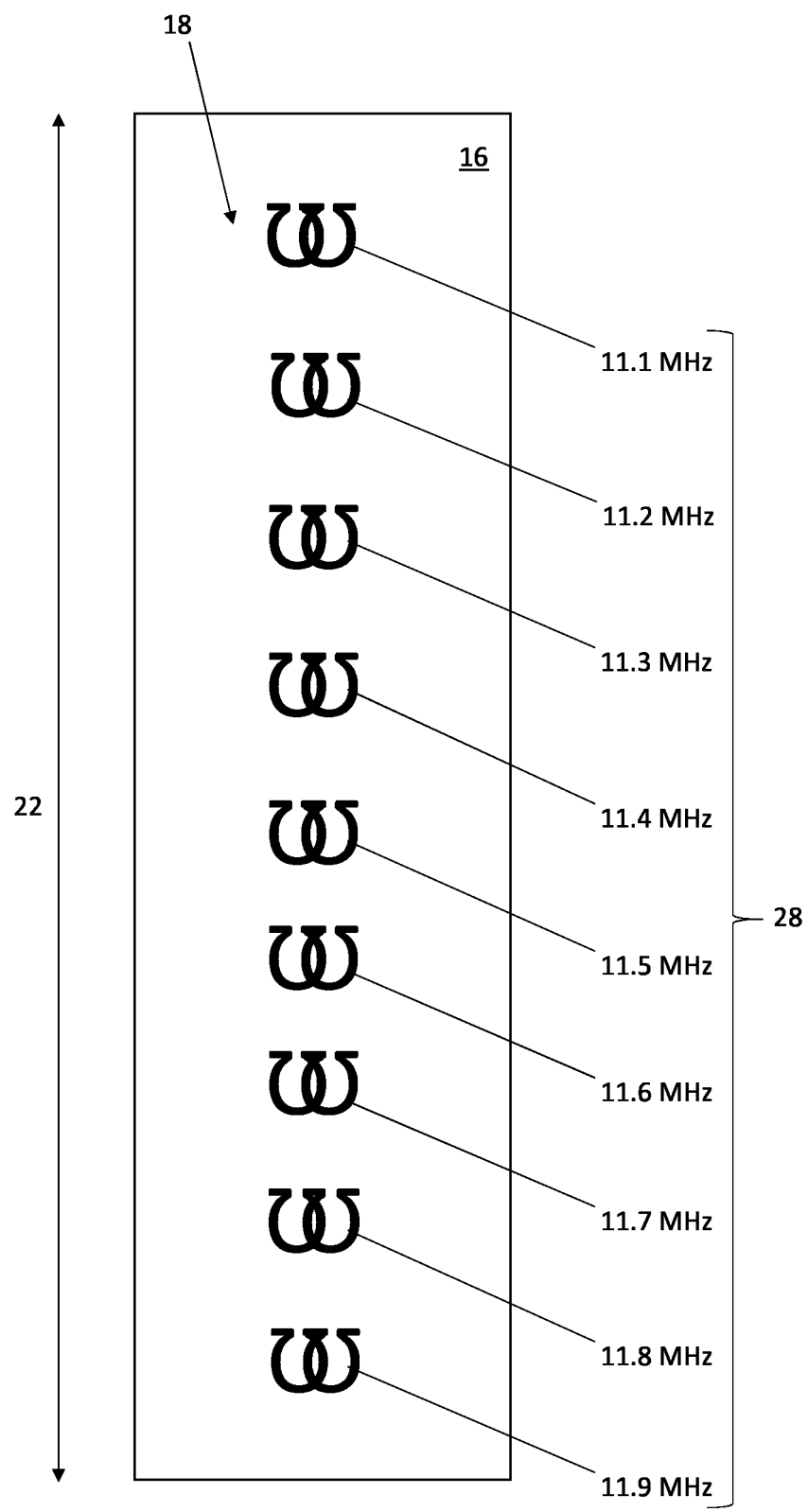
FIG. 3 is a close-up of a section of unrolled material to manufacture a diaper according to an embodiment of the present disclosure.

FIG. 3 is a close-up view of the plurality of printed tags 18 on the liquid impervious layer 16 of a diaper according to an embodiment of the present disclosure. As depicted, each tag 18 is printed and configured to operate with signal tuned to its respective specific frequency. Each tag is designed such that it is operable with respective dedicated frequency. In the depicted embodiment, nine tags are printed to operate with a set of frequencies ranging from 11.1 MHz to 11.9 MHz which form a plurality of pre-set frequencies 28. The range of 11.1 MHz to 11.9 MHz is provided for illustration purpose and any other range of frequencies can be used and is within the scope of this disclosure.

Figure 4:
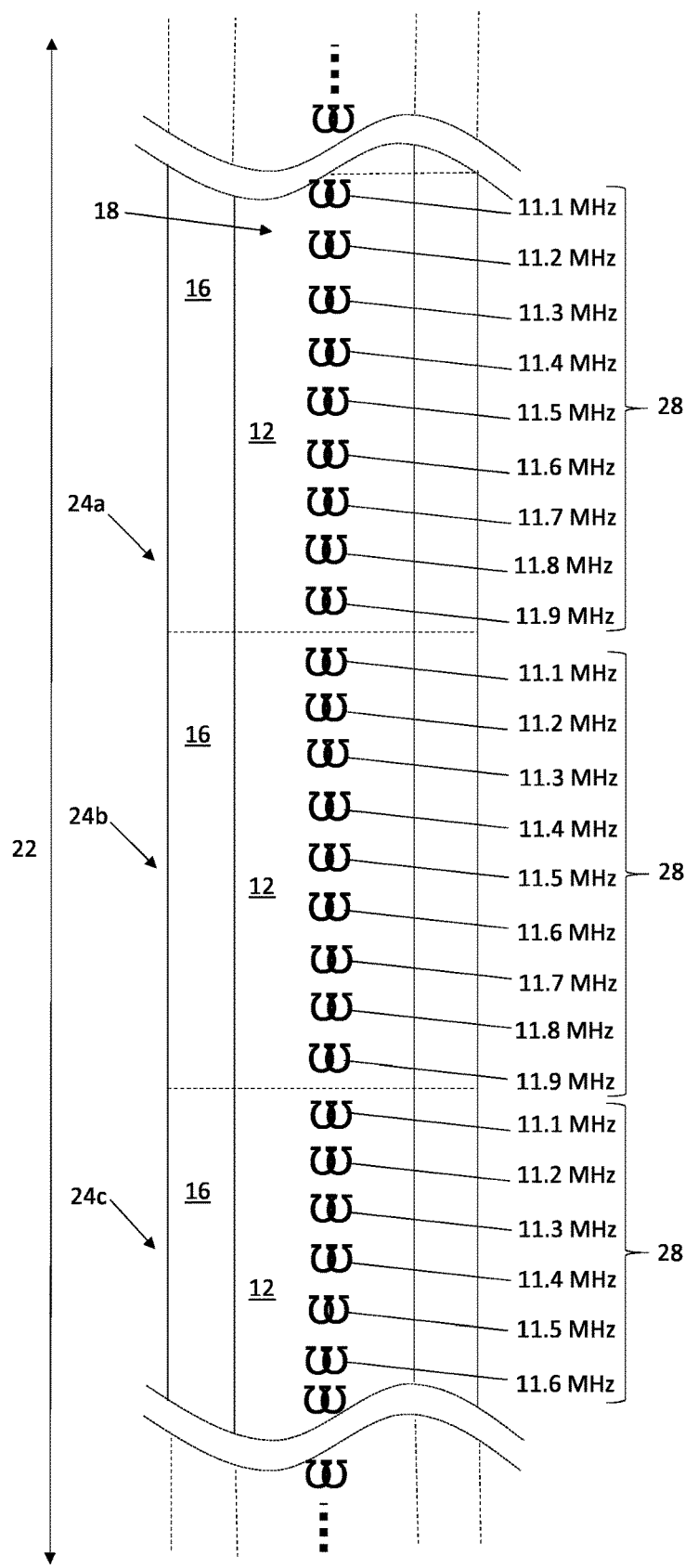
FIG. 4 is a schematic top view of another exemplary unrolled roll of material to manufacture diapers according to an embodiment of the present disclosure.

Moving to FIG. 4 that is an embodiment for explanation purpose of the principle, a roll 20 is represented with several sections of diaper material 24 ready to be cut at lines 26. Three sections 24a, 24b and 24c are represented. As one can appreciate, the plurality of tags 18 is (pre-)printed in order that each section 24 receives the same number of tags which will correspond to a same plurality of pre-set frequencies 28. As one can appreciate, the tags 18 are (pre-)printed in a way that ensures that the plurality of pre-set frequencies 28 is identically repeated on each section 24. As can be inferred, the same plurality of pre-set frequencies 28 is (pre-)provided again and again on every section 24. The result is that every diaper 10 will contain the same number of tags 18 corresponding to the same plurality of pre-set frequencies 28.

Figure 5:
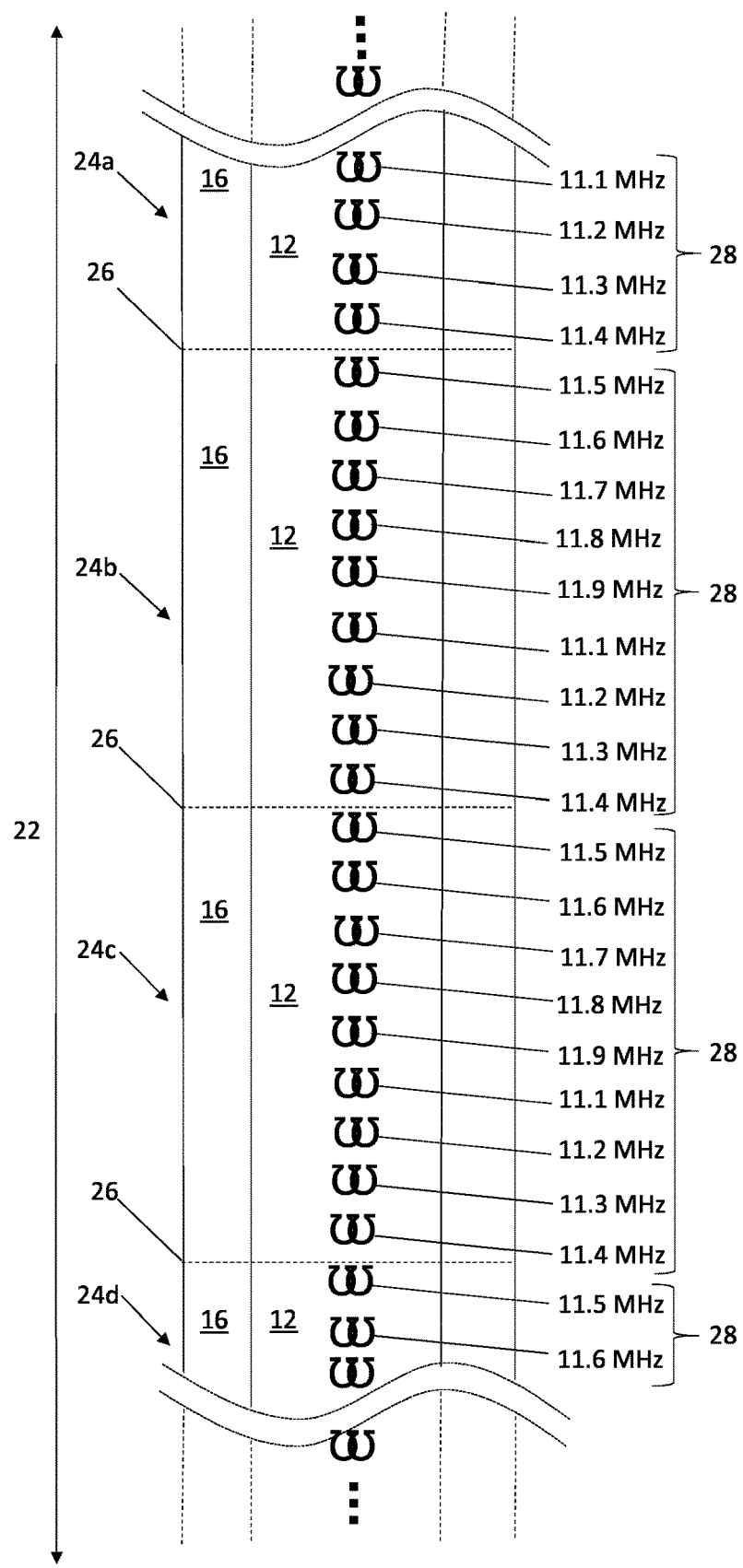
FIG. 5 is a schematic top view of further another exemplary unrolled roll of material to manufacture diapers according to an embodiment of the present disclosure.

Moving to FIG. 5, a particular situation is described as an example. Indeed, when the rolls 20 are unrolled, there is no guarantee that every section 24 will be cut so that the diaper will contain tags which will begin at 11.1 MHz and end at 11.9 MHz. The same serial of tags is provided endlessly, repeating the same plurality of pre-set frequencies 28. The purpose is that every section 24a, 24b, 24c and 24d will contain the same number of tags 18 and frequencies 28 though not necessarily starting at a specific frequency and ending at another specific frequency. In FIG. 5, the first tag of section 24b corresponds to the 11.5 MHz frequency. However, the cycle which ends at 11.9 MHz immediately restarts at 11.1 MHz ensuring the section 24b contains tags whose frequencies 28 range from 11.1 MHz to 11.9 MHz. As one can appreciate, sections 24a, 24b, 24c and 24d will have the same series of tags with the same plurality of pre-set frequencies 28. Every pre-set frequency 28 appears once, and only once, on every diaper 10. Every diaper 10 will have all the pre-set frequencies 28 printed on it.

Figure 6:
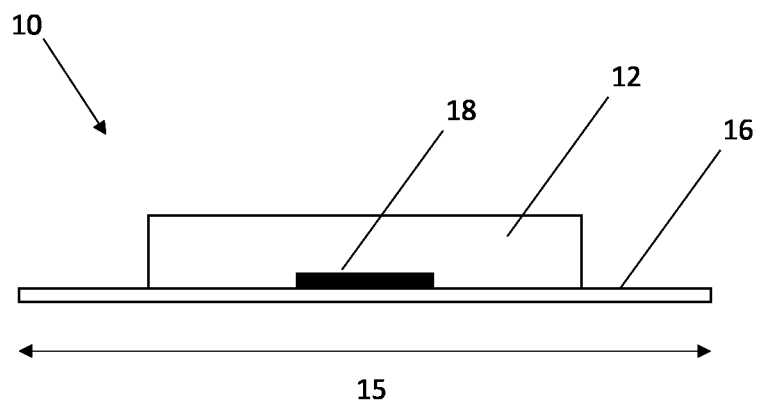
FIG. 6 is a schematic cross-section view of an exemplary diaper when no liquid is released in the diaper, according to an embodiment of the present disclosure.

FIG. 6 illustrates a schematic cross section view of a diaper 10 according to an embodiment of the present disclosure. For illustration purpose, the size of the different components was enhanced. There is at least one absorbent layer 12 that is disposed on top of at least one liquid-impervious layer 16. Tags 18 are printed on the layer 16. In an embodiment of the present disclosure, the tags 18 are printed on a longitudinal axis 22 that crosses width 15 of diaper 10 in the middle. It is understood that it is only an illustrative embodiment and that other possible dispositions for tags 18 are within the scope of this disclosure.

Figure 7:
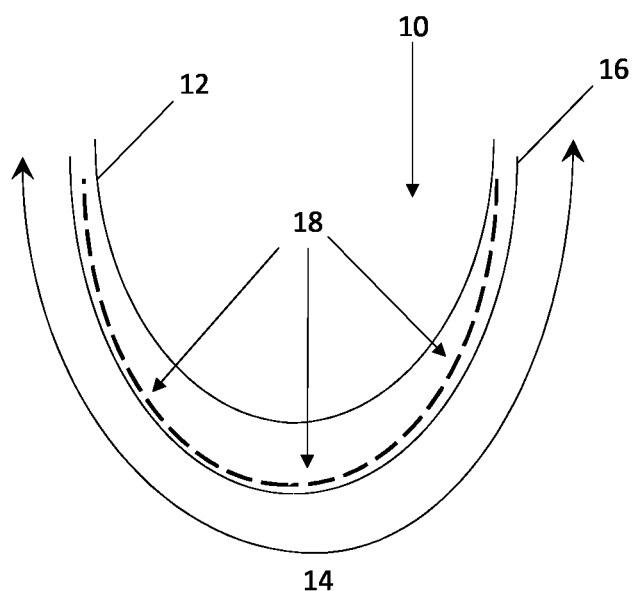
FIG. 7 is a schematic side cross-section view of an exemplary diaper when no liquid is released in the diaper, according to an embodiment of the present disclosure.

FIG. 7 illustrates a side cross section view of a diaper 10 according to an embodiment of the present disclosure and one can appreciate the disposition of the printed tags 18 on the length of the layer 16 with the absorbent layer 12 covering them.

Figure 8:
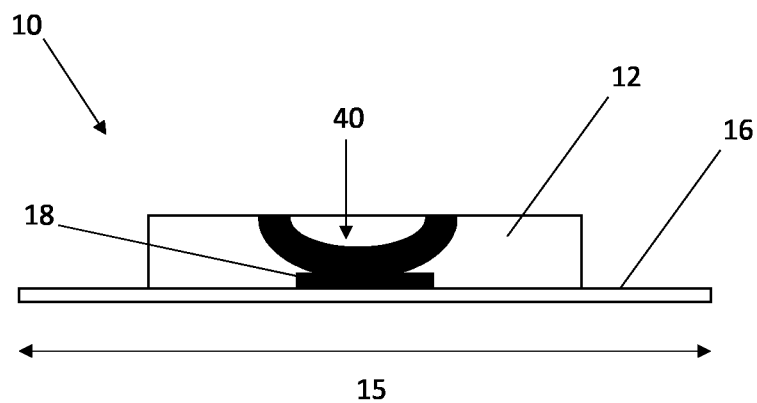
FIG. 8 is a schematic cross-section view of an exemplary diaper when liquid is released in the diaper, according to an embodiment of the present disclosure.
Figure 9:
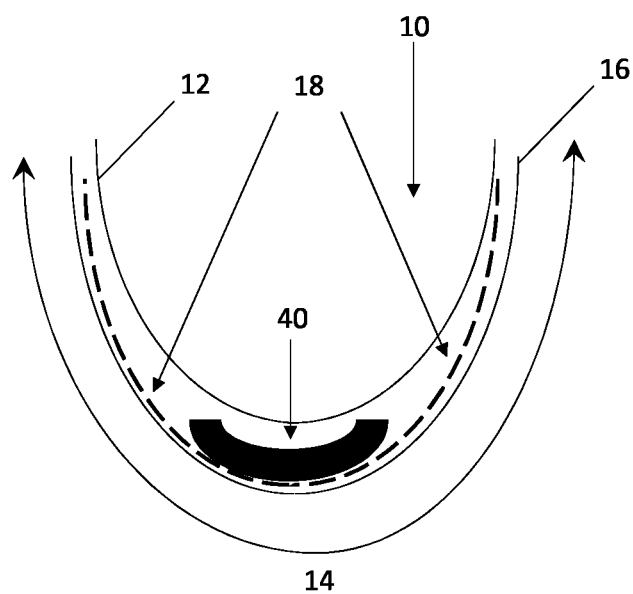
FIG. 9 is a schematic side cross-section view of an exemplary diaper when liquid is released in the diaper, according to an embodiment of the present disclosure.

Moving to FIGS. 8 and 9, they illustrate an exemplary diaper 10 when liquid 40 is released in it according to an embodiment of the present disclosure. One can appreciate that liquid 40 is absorbed in absorbent layer 12. Eventually, when the absorbent layer 12 moves toward saturation at the position of a tag 18 printed on the layer 16, the liquid will reach and get into contact with the tag 18. In FIG. 9, one can appreciate that as more liquid is absorbed in the absorbent layer 12, more and more tags 18 get in contact with the liquid 40. Eventually most or all tags 18 will be in contact with liquid 40.

For a tag 18 that is printed according to FIG. 1A, during its normal operation, the tag 18 receives a signal 36 tuned to its dedicated frequency f as transmitted by a transmitter 32 and resonates, i.e. the tag 18 is energized by the signal 36 transmitted by the transmitter 32. Then the tag 18 transmits a signal 38 back, also at its resonant frequency (i.e. its respective dedicated frequency f), but with a gradual decay, e.g. after the transmitter 32 stops emitting the signal 36.

On the other hand, when the tag 18 is in contact with liquid, the liquid will cause at least some of the exposed portions of the conductor 54 (and the conductor 74) to be short-circuited to each other, which results in the failure of the LC resonant circuit. Consequently, the tag 18 in contact with liquid cannot be energized by the signal 36 tuned to its dedicated frequency f and cannot transmit the signal 38 at that frequency back.

In such case, it is appreciated that the absence of the signal 38 (with gradual decay) tuned to a tag's dedicated frequency at a receiver 34 can be considered as the indication that that tag is in contact with liquid.

Figure 9A:
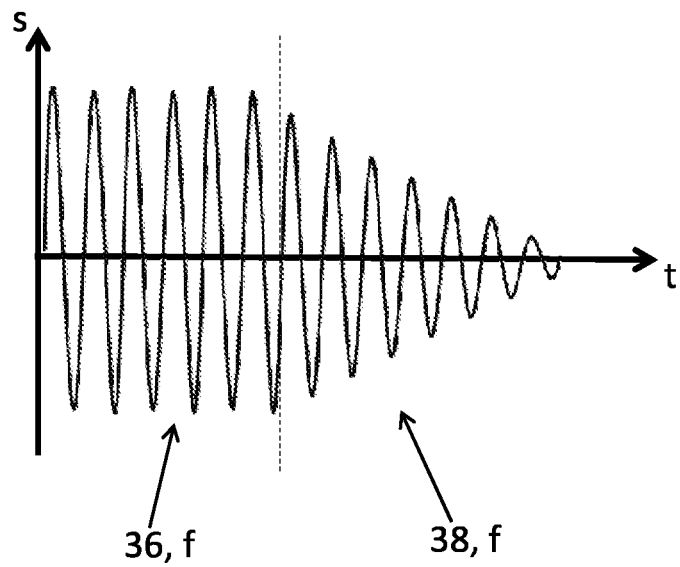
FIG. 9A illustrates an exemplary signal at the transceiver that transmits a signal with constant amplitude at a frequency f and receives a response from a resonating tag as manufactured in FIG. 1A, according to an embodiment of the present disclosure.

It is to be noted that the receiver 34 and the transmitter 32 can be embodied as a single unit, e.g. as a transceiver. In such case, the signal at the transceiver behaves in a manner as illustrated in FIG. 9A, in which the first part with constant amplitude represents the signal 36 transmitted by the transceiver 32/34 and the second part with a gradual decay represents the signal 38 received by the transceiver 32/34, i.e. as transmitted by the resonating tag. It is appreciated that the absence at the transceiver of the second part with a gradual decay can be used to indicate the failure of that specific tag, i.e. the contact of that tag with liquid.

As mentioned above, a diaper 10 is configured with a pre-determined number of tags 18, and each of the tags 18 is designed or configured to operate with its respective dedicated frequency f. Where the tags 18 in a diaper 10 are all printed according to FIG. 1A, each of the tags 18 is configured to respond to signal tuned to its dedicated resonant frequency f. In such case, a tag 18 can be determined to be in contact with liquid if no signal 38 (with gradual decay) at its resonant frequency is received at the receiver 34 after the transmitter 32 emits a signal 36 at the same resonance frequency. And based on the number and the locations of the tags in contact with liquid, the saturation level of the diaper 10 can be determined. For example, one frequency missing at the receiver, or two frequencies missing at the receiver that correspond to two tags 18 distant from each other cannot be considered as the indication to change the diaper, because that may be caused by error or only indicates small discrete liquid spot(s). On the other hand, e.g. four or five frequencies missing at the receiver that correspond to four or five consecutive adjacent tags 18 can be considered as indication to change the diaper.

It is appreciated that due to the manufacture variations and/or defects it is almost impossible to provide a tag with an exact nominal frequency. And even for a diaper with all tags of their exact nominal frequencies, the potential fold and/or pressure and/or shift might alter these frequencies when or during the diaper is worn. Therefore, in order for a better performance, it is preferable to determine, before the actual measurement of saturation level, the actual frequencies of the tags in a diaper already worn.

In order to avoid the need for such determination of the actual frequencies of the tags 18, a sweep of frequencies at least covering all the tags' nominal frequencies is transmitted by the transmitter 32, in an embodiment of the present disclosure. Note that the sweep of frequencies transmitted by the transmitter 32 has a higher resolution than the set of the nominal frequencies of the tags, that is, the interval between two sequential (adjacent) frequencies in the sweep transmitted by the transmitter 32 is much smaller than the interval between two sequential (adjacent) nominal frequencies of the tags 18. All the frequencies in the sweep other than those nominal ones are used to accommodate the potential variations or shifts or alterations in the actual frequencies of the tags 18.

Consider, as an example, an embodiment where nine tags 18 is embedded in a diaper 10 with their respective nominal frequencies of f1, f2, f3, . . . , f9, e.g. 10.1 MHz, 10.2 MHz, 10.3 MHz, 10.4 MHz, 10.5 MHz, 10.6 MHz, 10.7 MHz, 10.8 MHz, and 10.9 MHz. A sweep of frequencies at least covering all f1, f2, f3, . . . , f9, e.g. ranging from 9.9 MHz to 11.1 MHz is transmitted by a transmitter 32, with a resolution (i.e. the interval of two adjacent frequencies) of 0.001 MHz, i.e. 9.9 MHz, 9.901 MHz, 9.902 MHz, 9.903 MHz, . . . 10.604 MHz, 10.605 MHz, 10.606 MHz, . . . , 11.099 MHz, 11.1 MHz. In such case, there definitely exist nine frequencies in the sweep that (almost) perfectly match the actual frequencies of the nine tags 18, despite of the potential variation, shift or alteration in these nine frequencies.

Consider, as an example, an embodiment where the tags 18 are printed according to FIG. 1A. It is appreciated that without liquid it is expected to have nine frequencies (i.e. the actual resonant frequencies of the nine tags 18) to appear at the receiver 34, and thus it is possible to determine the saturation level of the diaper 10 based on the number of the frequency/frequencies missing at the receiver 34 and the location(s) of the corresponding tag(s). For example, one frequency missing at the receiver, or two frequencies missing at the receiver that correspond to two tags 18 distant from each other cannot be considered as the indication to change the diaper. On the other hand, e.g. four or five frequencies missing at the receiver that correspond to four or five consecutive adjacent tags 18 can be considered as indication to change the diaper.

Figure 9B:
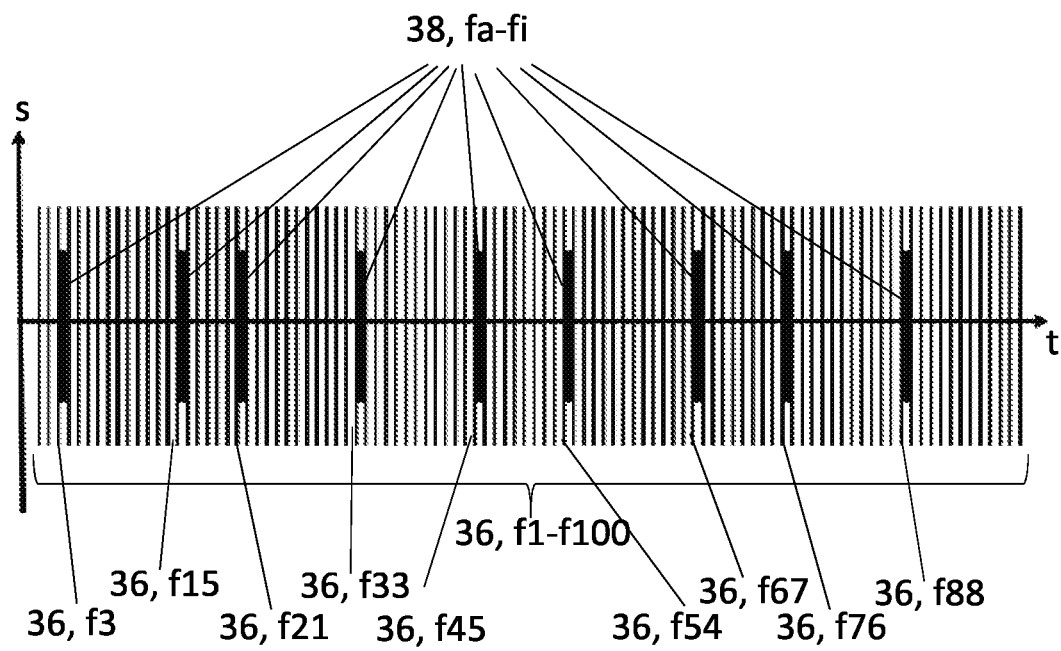
FIG. 9B illustrates a graph of an exemplary signal at a transceiver when a swept frequency is transmitted according to an embodiment of the present disclosure.

FIG. 9B illustrates a graph of an exemplary signal at a transceiver when a sweep of frequencies is transmitted according to an embodiment of the present disclosure. In the illustrated embodiment, there exist nine tags in a diaper, and a sweep of frequencies f1-f100 (in particular, 100 signals 36 each of which is tuned to one of the frequencies f1-f100) covering the nominal resonant frequencies of the nine tags is transmitted by the transceiver 32, as an example. When there is no liquid in the diaper, the nine tags resonate at their respective resonant frequencies and each resonating tag transmits back a signal 38 at its respective resonant frequency. As illustrated, nine signals 38 appear at the transceiver at the frequencies fa-fi, that is, the actual resonant frequencies of the nine tags are fa, fb, . . . , fi respectively. In the example as illustrated in FIG. 9B, the frequencies fa, fb, fc, fd, fe, ff, fg, fh, and fi correspond to frequencies f3, f15, f21, f33, f45, f54, f67, f79 and f88 respectively.

As mentioned above, when a signal 38 e.g. at frequency fc (equivalent to f21) is missing at the transceiver, the tag 18 with actual resonant frequency fc can be determined to be in contact with liquid. Therefore, based on the number of the signal(s) 38 missing at the receiver/transceiver and based on the location(s) of the corresponding tags, it is possible to determine the saturation level of the diaper. Note that in order to determine the saturation it is not necessary to first determine the actual resonant frequencies of the tags. Instead, the saturation can be estimated without determining the actual resonant frequencies of the tags, i.e. by determining the intact tag(s) based on the frequencies appearing at the receiver, and then determining the saturation based on the locations of the other missing frequencies.

Consider, as an example, an embodiment where a set of a pre-determined number of tags 18 with ascending/descending frequencies is continually repeatedly printed in the same arrangement on the liquid-impervious material/layer. Where the diapers are manufactured (i.e. the combined material rolls such as the absorbent material roll and the liquid-impervious material roll are cut) in such a manner that one such set of the pre-determined number of tags 18 with ascending/descending frequencies is contained right in a diaper as manufactured, it is simple and intuitive to determine the saturation of the diaper because the tags are arranged sequentially and consecutively with frequencies ascending/descending from one end to the other end of the diaper along its length. That is, along the diaper's length, the tag associated with the highest frequency is located closest to one end of the diaper, while the tag associated with the lowest frequency is located closest to the other end of the diaper, and therebetween the frequencies of the tags descend from the one end to the other end. Consequently, the absence at the receiver of the signal tuned to the nth highest frequency indicates the nth tag from the one end of the diaper is in contact with liquid and two consecutive adjacent frequencies are associated with two consecutive adjacent tags.

However, as mentioned above, during the diaper manufacture it is possible for the diaper to be manufactured such that the resonant frequencies do not ascend/descend from one end to the other end of the diaper along its length. As an example, the diapers may be manufactured (i.e. the combined material rolls such as the absorbent material roll and the liquid-impervious material roll are cut) in such a manner that the tag associated with the nth highest frequency is located closest to one end of the diaper, while the tag associated with the (n+1)th highest frequency is located closest to the other end of the diaper, and therebetween from the one end to the other end, the frequencies of the tags ascend from the (n−1)th highest frequency to the highest frequency, jump to the lowest frequency, and then ascend to the (n+2)th highest frequency. In such case, there exists a frequency jump between two consecutive adjacent tags in a diaper, which shall be taken into account for the determination of saturation. In particular, the two tags related to the frequency jump shall be considered as two consecutive adjacent tags.

Figure 10A:
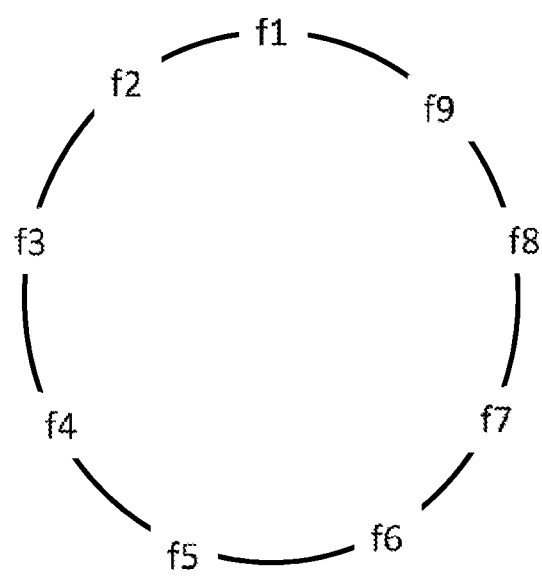
FIG. 10A illustrates graphically the rollover of the frequencies in sequence, according to an embodiment of the present disclosure.

In an embodiment of the present disclosure, the set of the pre-determined number of tags is considered as being arranged in a loop, i.e. the last tag in the set is considered to be followed by the first tag in the set, for which an example is illustrated in FIG. 10A where nine tags (and also nine frequencies) are included in the set. In this way, no matter between which two consecutive adjacent tags the material rolls are cut, we can determine from such loop the actual set of tags in a manufactured diaper. Accordingly, the actual set of the corresponding frequencies (e.g. the resonant frequencies) can be determined from such loop. By doing so, the adjacency relations can be determined among the tags and among the frequencies in a diaper, which is useful in determining the saturation of the diaper, i.e. whether the several areas that are deemed to be wet are consecutive and adjacent.

Figure 10:
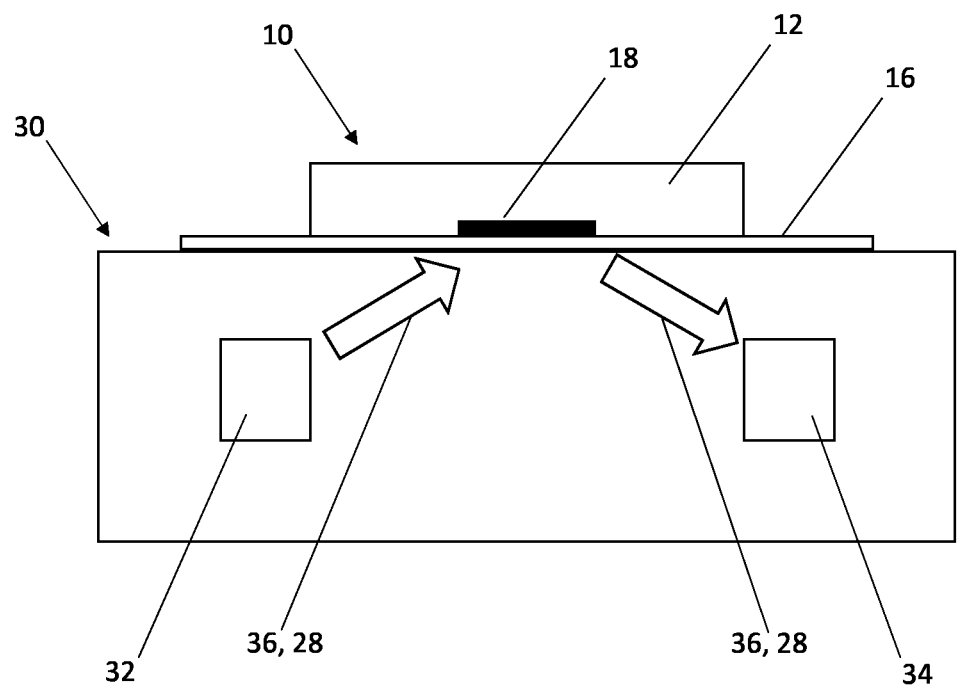
FIG. 10 is a schematic cross section view of an exemplary diaper on an equipped bed when no liquid is released in the diaper, according to an embodiment of the present disclosure.

Moving to FIG. 10, an exemplary diaper 10 is situated on a bed 30, according to an embodiment of the present disclosure. It is to be noted that it is also possible for the diaper of the present disclosure to be used with other equipment such as e.g. chair or else, which shall be considered to be within the scope of the present disclosure.

The bed 30 is equipped with a transmitter 32 and a receiver 34. In this embodiment, the transmitter 32 and the receiver 34 are embedded in the bed 30, but other possible embodiments are considered within the scope of this disclosure. In FIG. 10, the transmitter 32 and the receiver 34 are illustrated to be arranged on the opposite sides relative to the diaper 10. It is to be noted that this arrangement is for illustrative purpose only, and the transmitter 32 and the receiver 34 can be disposed in any arrangement relative to the diaper 10 (in particular, the tags 18) that enables the tags 18 in the diaper 10 to resonate with signal tuned to their respective dedicated frequency transmitted from the transmitter 32 and transmit signal at their respective dedicated frequency back to the receiver 34 (if the tags are designed to do so), to relay or reflect towards the receiver 34 the wireless signal at their respective dedicated frequency transmitted from the transmitter 32 (if the tags are designed to relay or reflect signal tuned on their respective dedicated frequency), or to absorb or interfere with the wireless signal at its respective dedicated frequency transmitted from the transmitter 32 that would otherwise be received by the receiver 34 (if the tags are designed to absorb or interfere with the signal tuned on their respective dedicated frequency), e.g. the transmitter 32 and the receiver 34 can be arranged on the same side relative to the diaper 10, e.g. both on the left side or both on the right side.

A wireless signal 36 is emitted from the transmitter 32 at the dedicated frequency 28 of a tag 18. Now because of no urination or defecation yet, the tag 18 is not in contact with any liquid, and thus operates as configured. That is, the tag 18 relays or reflects the wireless signal 36 at the frequency 28 toward the receiver 34 if the tags printed on the liquid-impervious layer 16 are designed to relay or reflect the waves set on a specific frequency, as illustrated in FIG. 10. Alternatively, if the tags printed on the liquid-impervious layer 16 are designed to absorb or interfere with the waves set on a specific frequency, the tag 18 absorbs or interferes with the wireless signal 36 when not in contact with any liquid, not illustrated in the drawings. Similarly, the tag 18 resonates with the signal 36 and transmits back signal 38 at the frequency 28 if the tags printed on the liquid-impervious layer 16 are designed to resonate with and transmit back signal at their respective frequency, also not illustrated in the drawings. There is no need for a direct contact between the transmitter and receiver and the diaper. As one can appreciate from FIG. 10 and the followings, the process to detect and monitor the presence of liquid is wireless and remote. This process is repeated for every tag 18 printed in the diaper 10. Further details will be provided with next figures.

Figure 11:
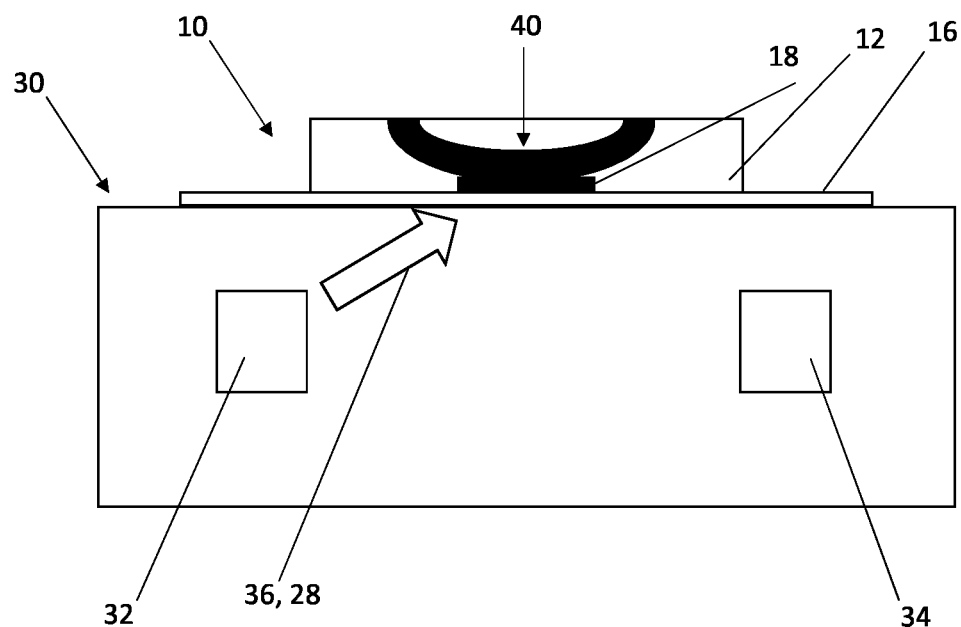
FIG. 11 is a schematic cross section view of an exemplary diaper on an equipped bed when liquid is released in the diaper, according to an embodiment of the present disclosure.

In FIG. 11, liquid 40 has been released in the diaper 10 and expands. The tag 18 visible on FIG. 11 is in contact with liquid 40 at this time, which prevents the tag 18 from operating as designed or configured. That is, when the transmitter 32 emits signal 36 at the frequency 28, the tag 18, if designed to relay or reflect the waves set at the frequency 28, does not relay or reflect the signal 36 towards the receiver 34 due to its contact with liquid 40, and thus the receiver 34 fails to receive the wireless signal 36 at the frequency 28, as illustrated in FIG. 11. Alternatively, if the tags printed on the liquid-impervious layer 16 are designed to absorb or interfere with the waves set on a specific frequency, the tag 18 does not absorb or interfere with the wireless signal 36 due to its contact with liquid, and thus the receiver 34 receives the wireless signal 36 at the frequency 28, not illustrated in the drawings. Similarly, if the tags printed on the liquid-impervious layer 16 are designed to resonate with and transmit back signals tuned to their respective dedicated frequency, the tag 18 does not resonate with the wireless signal 36 and thus does not transmit back signal 38 at its frequency, due to its contact with liquid, and consequently the receiver 34 does not receive the wireless signal 38 at the frequency 28, not illustrated in the drawings. The absence (when the tags are designed to relay or reflect the wireless signal, as illustrated in FIG. 11, or to resonate with and transmit back signal, not illustrated in the drawings) or presence (when the markers are designed to absorb or interfere with the wireless signal, not illustrated in the drawings) of the wireless signal at the frequency of tag 18 on the receiver 34 indicates the liquid reached the tag 18 and the absorbent layer has reached a level of saturation corresponding to said tag position in the diaper 10.

Figure 12:
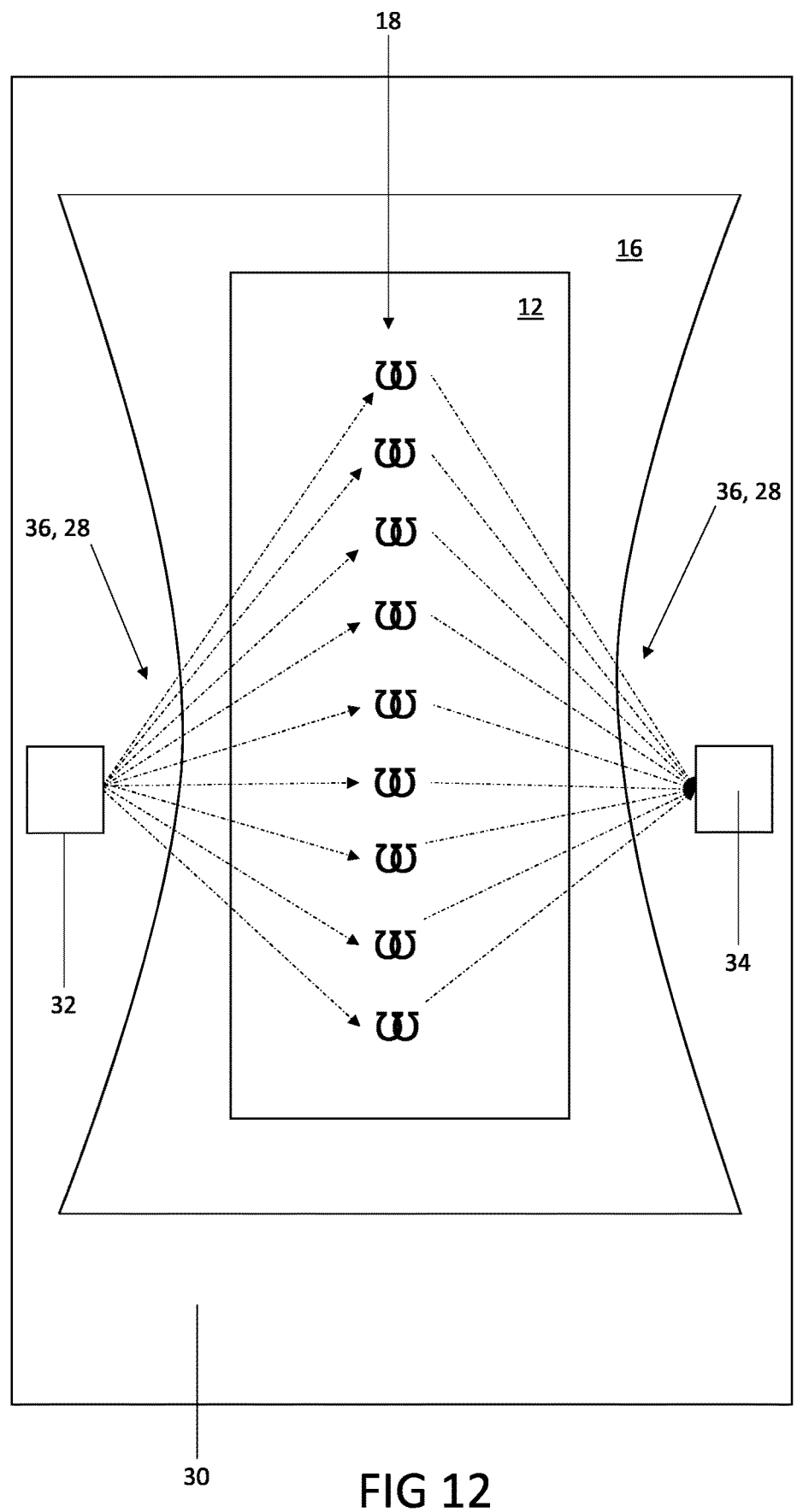
FIG. 12 is a schematic top view of an exemplary diaper on an equipped bed when no liquid is released in the diaper, according to an embodiment of the present disclosure.

Moving to FIG. 12, an exemplary diaper 10 is positioned on an equipped bed 30 according to an embodiment of the present disclosure. The transmitter 32 transmits a plurality of signals 36 tuned on the pre-set frequencies 28. When the signal 36 tuned at a specific frequency 28 arrives at the corresponding tag 18 that is designed to relay or reflect (as illustrated in FIG. 12) or to absorb or interfere with (not illustrated in the drawings) or to resonate with (not illustrated in the drawings) the signal at the specific frequency 28, that tag 18 relays or reflects (as illustrated in FIG. 12) or absorbs or interferes with (not illustrated in the drawings) the signal 36 tuned at the specific frequency 28 or resonates and transmits back a signal 38 at the specific frequency 28 (not illustrated in the drawings) if that tag 18 is dry, which results in the signal 36/38 tuned at the specific frequency 28 being (as illustrated in FIG. 12) or not being (not illustrated in the drawings) received by the receiver 34.

Figure 13:
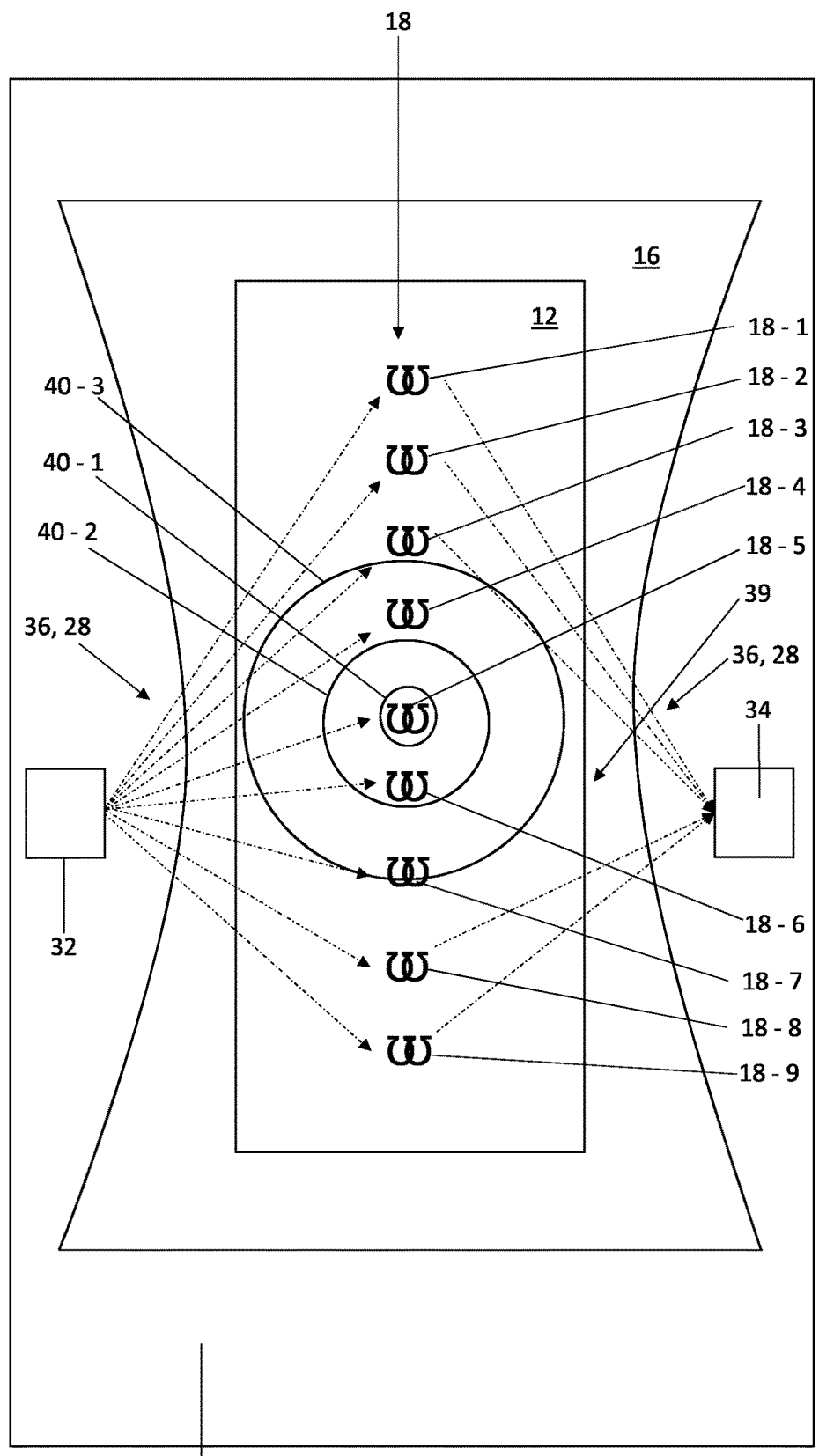
FIG. 13 is a schematic top view of an exemplary diaper on an equipped bed when liquid is released in the diaper, according to an embodiment of the present disclosure.

Moving to FIG. 13, liquid 40 has been released in diaper 10. Also the transmitter 32 emits the plurality of signals 36 tuned on the pre-set frequencies 28. Tags 18 that are situated toward the extremities of the diaper 10 are not in contact with the liquid and thus still capable to operate as designed or configured, i.e. relay or reflect (as illustrated in FIG. 13) or absorb or interfere with (not illustrated in the drawings) the signal 36 at its respective frequency 28 or resonate with the signal 36 and transmit back a signal 38 at the same frequency 28 (not illustrated in the drawings), and thus the receiver 34 still receives (as illustrated) or does not receive (not illustrate) said signal 36/38. However, one can appreciate that several tags 18 are caught in the pool of liquid 40. The presence of liquid 40 makes these tags 18 not able to operate as designed or configured. As illustrated in FIG. 13, in an embodiment where the tags are designed to relay or reflect the signal at a specific frequency, the tags that are caught in the pool of liquid 40 cannot any more relay or reflect the signals 36 towards the receiver 34. The empty area 39 visually represents these "cone of silence" where the interrupted signals that receiver 34 should have received are absent. One can appreciate with FIG. 13 that, as the liquid will expand further into the diaper 10, more tags 18 will be exposed to it and won't operate as designed or configured, e.g. won't relay or reflect or resonant with (or won't absorb or interfere with) the signals 36. As a result, the receiver 34 will receive less signals 36/38 than departing signals 36 sent by transmitter 32 (in case that the tags are designed to relay, or reflect, or resonate with and transmit back) or receive more signals 36 than expected (in case that the tags are designed to absorb or interfere with). Since each tag has its own frequency 28, one can discriminate between the signal from a tag 18 (e.g. situated in the center of the diaper 10) and another tag 18 (e.g. situated at the extremity of the diaper 10). Hence, based on the frequencies received by receiver 34 and the respective positions of their corresponding tags 18, it is possible to monitor the liquid's progress in the diaper and the level of saturation until the diaper has to be changed.

As an example, in the embodiment illustrated in FIG. 13 where the tags are designed to relay or reflect the signal at their respective specific frequencies, for the first urination 40-1 only the tag 18-5 is in contact with the liquid, and thus only signal 36 at the frequency associated with that tag 18-5 is absent at the receiver 34, which implies that the diaper 10 is already wet but not saturated enough for change. Then after the second urination 40-2, the tags 18-5 and 18-6 are both in contact with the liquid, and thus the signals 36 at both the frequency associated with the tag 18-5 and the frequency associated with the tag 18-6 are absent at the receiver 34, which indicates that the diaper 10 is more wet but still not saturated enough for change. After the third urination 40-3, the tags 18-4, 18-5, 18-6 and 18-7 are all in contact with the liquid and thus the signals 36 at all the frequencies associated with these four tags are absent at the receiver 34, as illustrated in FIG. 13. The absence of the four signals 36 at the four frequencies may be considered as the indication to change the diaper 10. It can be understood from the above that it is possible to monitor the diaper's saturation based on the missed frequencies at the receiver 34.

It is appreciated that the wireless signal might be blocked by the body of the diaper wearer. Consequently, it is possible for a signal missing at the receiver to result from the block by the body, instead of from the normal operation of an intact tag (in the case where the tag is configured to absorb or interfere with the signal tuned to its dedicated frequency) or from the failure of a tag in contact with liquid (in the case where the tag is configured to resonate and re-transmit, or relay, or reflect the signal tuned to its dedicated frequency).

To avoid any potential negative impact from the block of the body, in an embodiment of the present disclosure, more than one pair of a transmitter and a receiver is deployed around the diaper wearer in a manner that ensures for any tag in the diaper at least one signal path from the transmitter and at least one signal path to the receiver is not blocked by the body. The more than one pair deployed around the diaper wearer can be configured to share information with each other, e.g. communicate with each other, so as to make the correct decision even when some missing signal(s) results from the block by the body.

Figure 14:
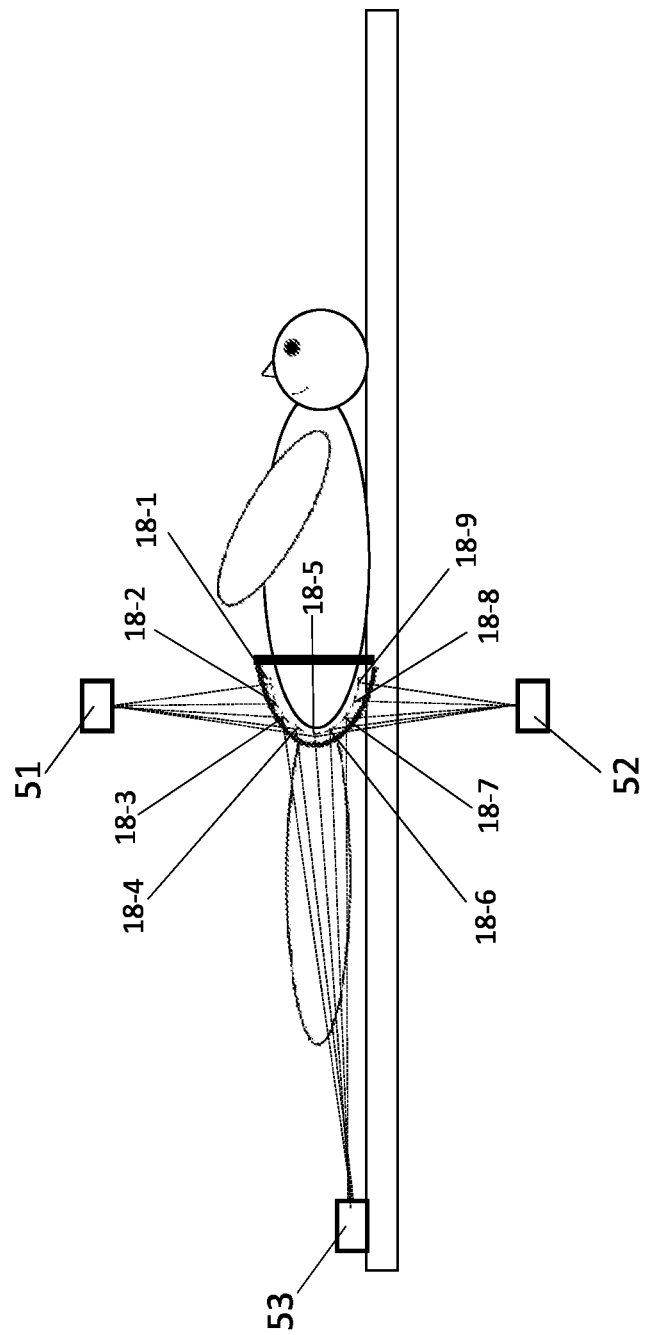
FIG. 14 illustrates a schematic diagram of a wetness detection system according to an embodiment of the present disclosure.

FIG. 14 outlines a schematic diagram of a wetness detection system according to an embodiment of the present disclosure, where three transceivers 51, 52 and 53 are deployed around the lower body (in particular, the diaper) of a diaper wearer who is lying on a bed. As illustrated, the transceivers 51 and 52 are deployed over and underneath the diaper wearer's lower body (e.g. directly over and underneath the diaper worn by the wearer), while the transceiver 53 is deployed to be aligned with the upper surface of the bed and to point towards the diaper wearer's feet (in particular, towards the bottom of the diaper worn by the wearer). It is appreciated that these three transceivers 51, 52, and 53 in a whole can transmit/receive signal to/from any of the tags in the diaper, without block or interruption by the diaper wearer's body.

As an example, nine tags 18, i.e. 18-1, 18-2, ... , 18-9, are provided in the diaper worn by the diaper wearer, and three transceiver 51, 52 and 53 are deployed around the diaper, as illustrated in FIG. 14. It is illustrated in FIG. 14 that the signal paths between the transceiver 51 and the tags 18-6, 18-7, 18-8, and 18-9, the signal paths between transceiver 52 and the tags 18-1, 18-2, 18-3, and 18-4, as well as the signal paths between the transceiver 53 and the tags 18-1, 18-2, 18-8, and 18-9 are blocked by the diaper wearer's body as an example. In the worst case, the signals on these blocked signal paths are completely blocked, and thus regardless of whether or not the corresponding tag is in contact with liquid, the transceiver 51 will not receive any signals from tags 18-6, 18-7, 18-8, and 18-9, the transceiver 52 will not receive any signals from tags 18-1, 18-2, 18-3, and 18-4, while the transceiver 53 will not receive any signals from tags 18-1, 18-2, 18-8, and 18-9. Therefore, when working individually and independently, each of these three transceivers might arrive at a wrong conclusion when determining the presence of liquid. However, when the three transceivers share information with each other, they will arrive at the correct conclusion.

When the wearer puts on a diaper, the diaper is scrunched between the wearer's legs, which results in some folds in the diaper that in turn might cause the failure of some tags in the diaper. It is noted that in general the folds are along the length 14 of the diaper because the wearer always pulls up the diaper as far as possible to avoid its potential sliding down which also avoid any transverse fold. To eliminate or mitigate the negative impact from the longitude fold, multiple (e.g. three or four) columns of tags are provided in the diaper along its length 14 according to an embodiment of the present disclosure. With the multiple columns of tags in the diaper, even with the scrunching of the diaper between the legs and the fold(s) caused thereby, at least one tag in each row (i.e. along the width 15) will function as normal, so as to indicate the presence or absence of liquid at that row.

Figure 15:
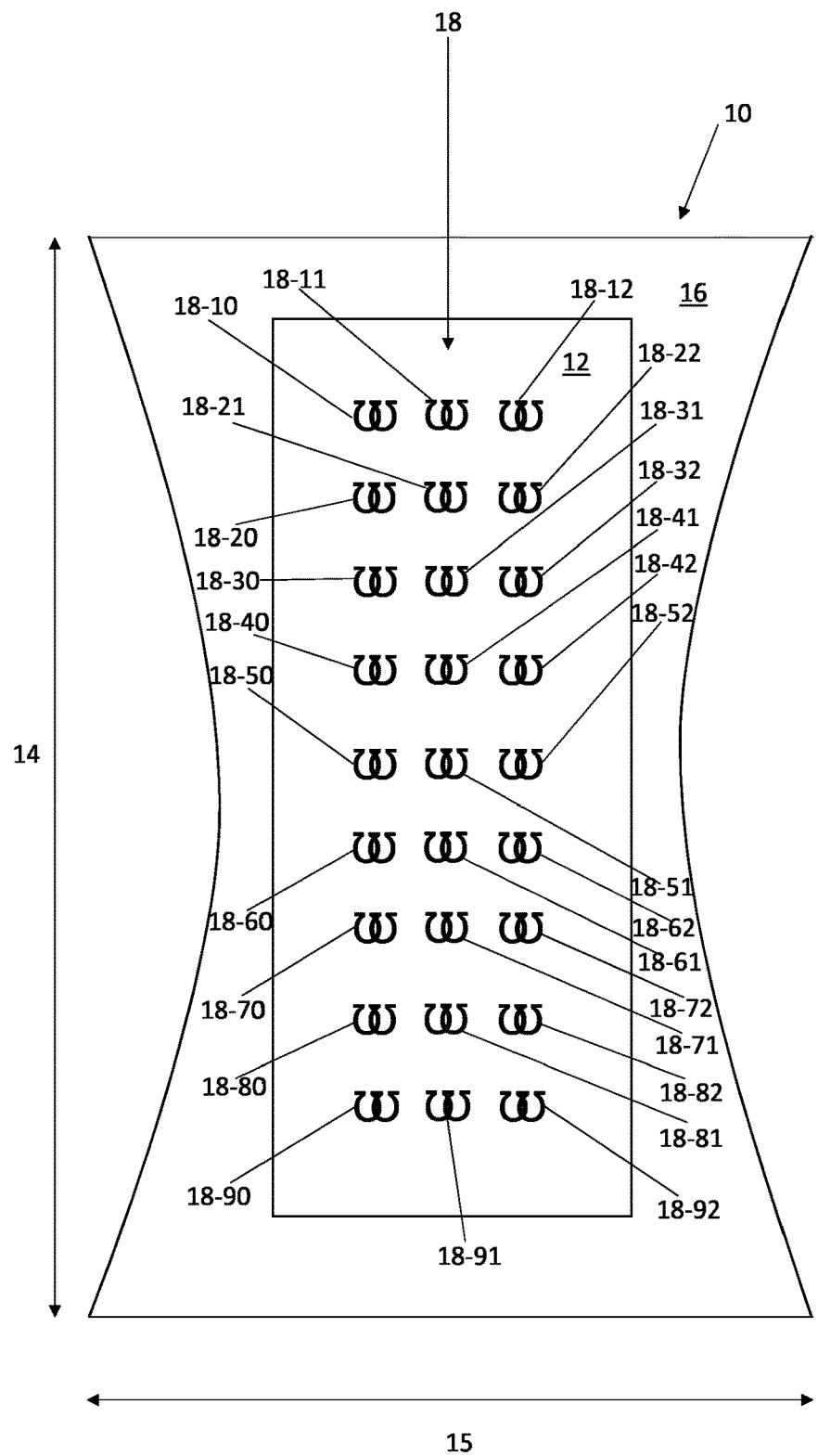
FIG. 15 illustrates a schematic diagram of a diaper with more than one (e.g. three) columns of tags according to an embodiment of the present disclosure.

For example, in the embodiment as illustrated in FIG. 15, although the scrunching or the fold(s) of the diaper results in the failure of tags 18-40, 18-41, 18-51, 18-52, 18-60, and 18-62, the tags 18-42, 18-50, and 18-61 still function as normal, i.e. resonate with or relay or reflect or absorb or interfere with the signals tuned to their dedicated frequencies respectively when intact and not do so when in contact with liquid. Therefore, even with scrunching and fold(s), it is still possible to determine, based on the signal at the receiver, whether or not liquid exists in the respective row, that is, a row will be determined to be wet only when all the tags in that row do not operate as configured or designed. And only when all the tags in several (e.g. 4, 5, or 6) consecutive (adjacent) rows do not operate as configured or designed, the diaper can be determined to be saturated, and thus need to be change.

Figure 15A:
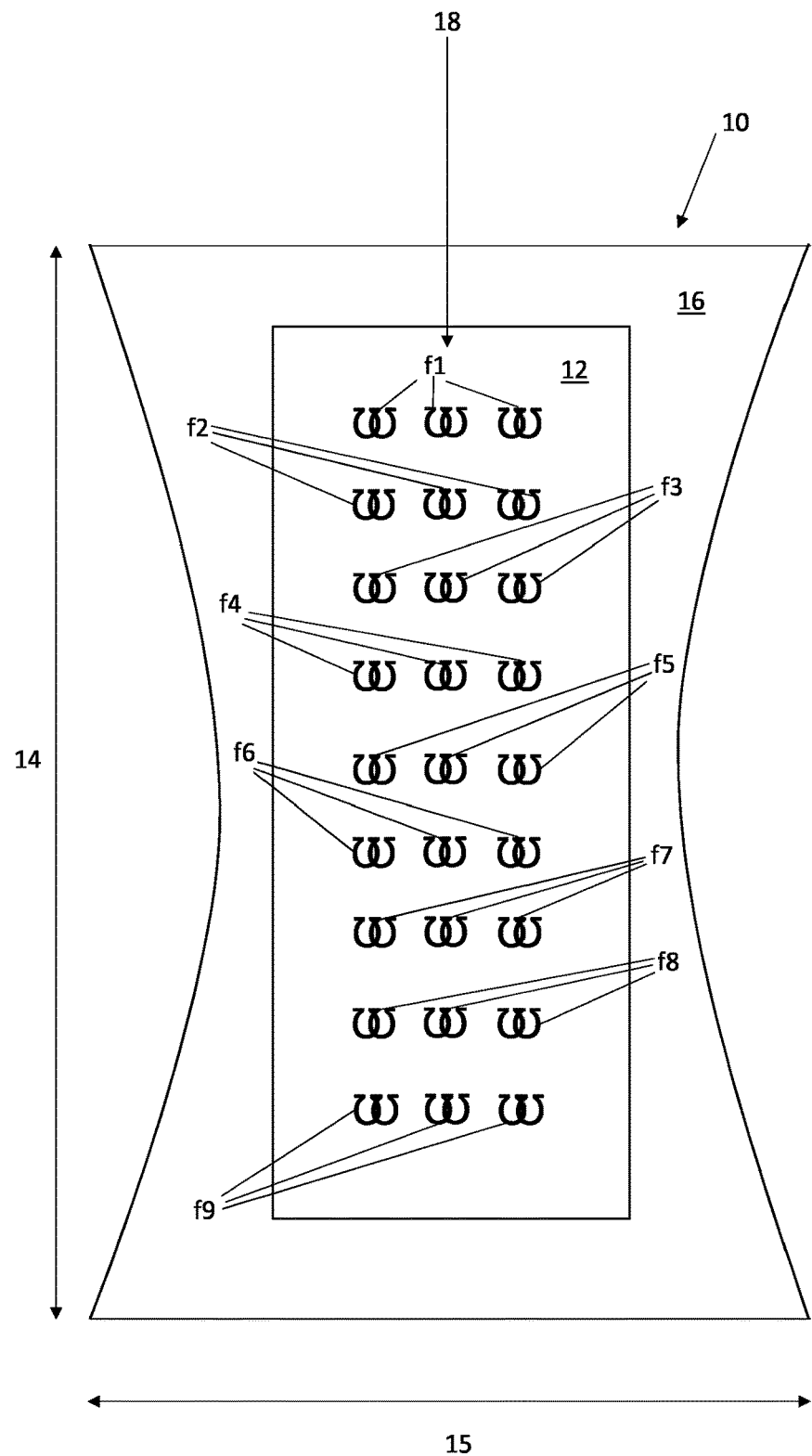
FIG. 15A and FIG. 15B illustrates two exemplary frequency distributions of the tags in the diaper as illustrated in FIG. 15, according to an embodiment of the present disclosure.

As an example, all tags in a row are associated with a same frequency and different rows of tags are associated with different frequencies, in which case a row will be determined to be wet only when the expected signal behavior responding to the signal tuned to that row's corresponding frequency is missing at the receiver. FIG. 15A illustrates a schematic diagram of a diaper with three columns of tags 18 according to an embodiment of the present disclosure, in which all the three tags in a row are associated with a same frequency and different rows are associated with different frequencies.

Figure 15B:
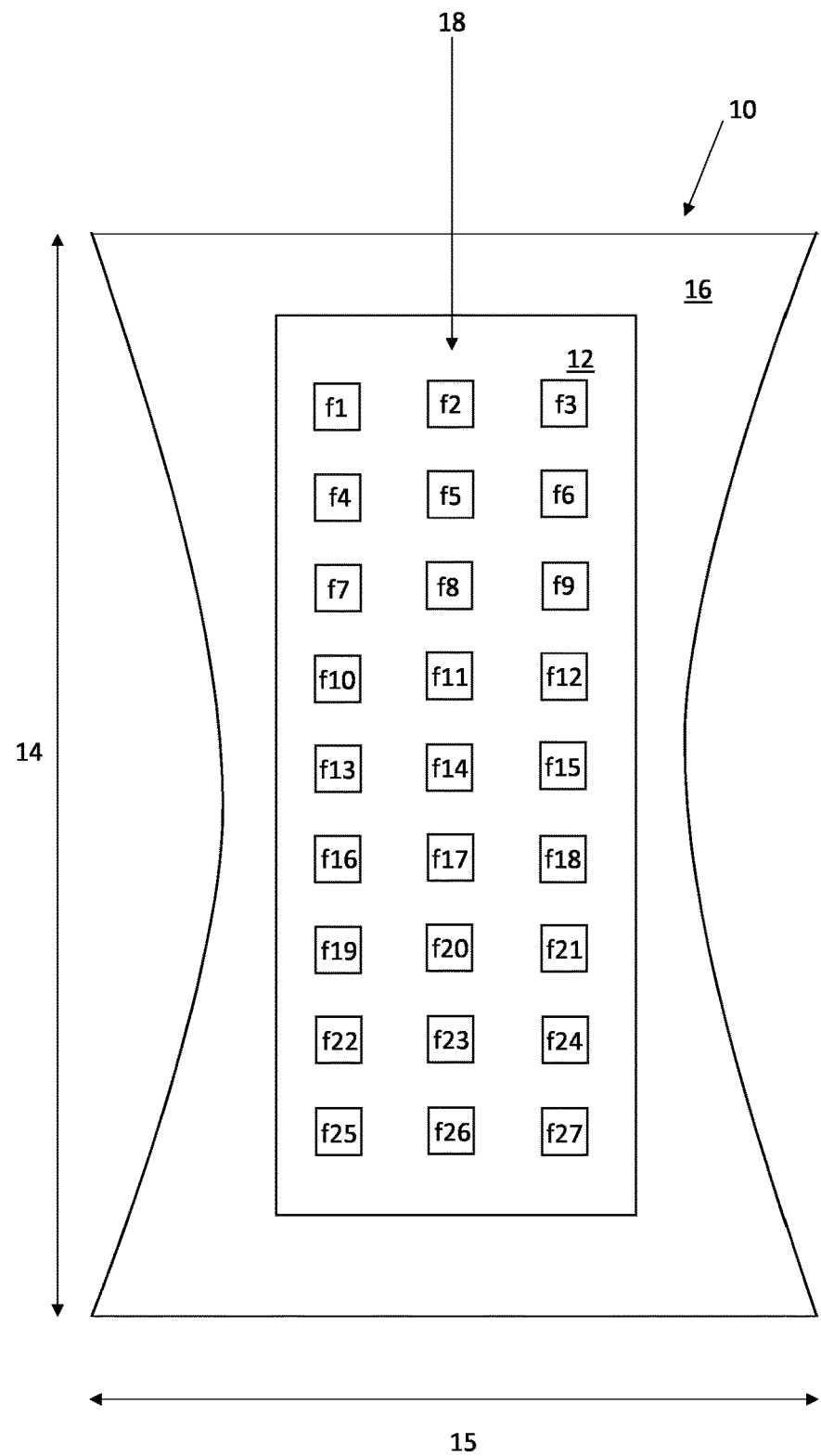

Alternatively, the frequencies of the tags in the diaper may be made more random in order to have a better immunity to the noise. For example, at least in an area of a diaper all the frequencies of the tags are different. In that area, the frequencies of all the tags in a row are different from each other. Also, as mentioned above, it is practical for the frequencies of the tags in a column to be consecutive, i.e. either ascend or descend, so as to facilitate the printing procedure of the tags. FIG. 15B illustrates a schematic diagram of a diaper with three columns of tags 18 according to an embodiment of the present disclosure, in which all tags in the diaper are associated with different frequencies.

Figure 15C:
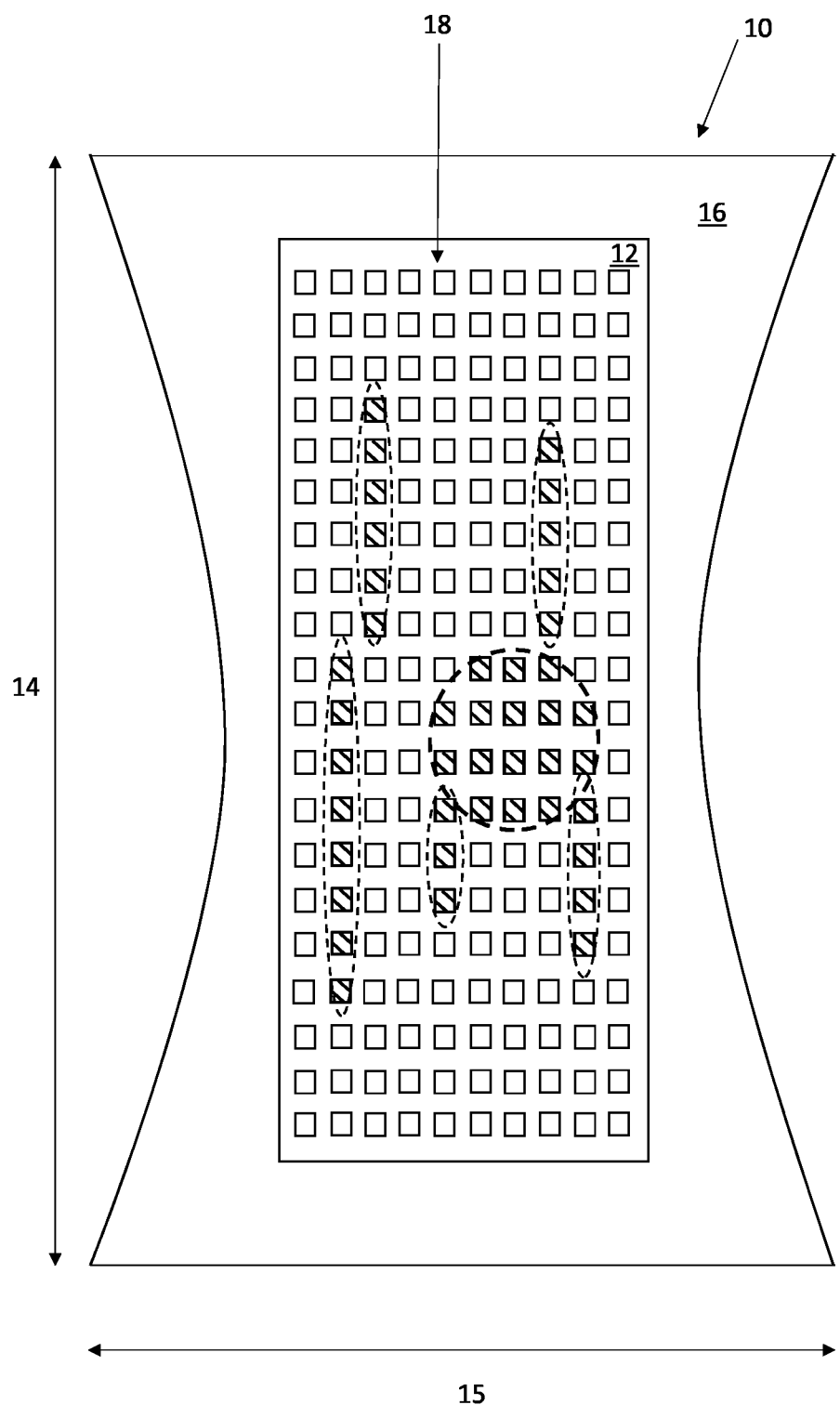
FIG. 15C illustrates a schematic diagram of a diaper with tags provided throughout the liquid-impervious layer, according to an embodiment of the present disclosure.

In another embodiment of the present disclosure, the tags are printed throughout a (either inner or outer) side of the liquid-impervious layer, e.g. in a 10×20 array with all tags (i.e. frequencies) being different from each other. FIG. 15C illustrates a signal distribution diagram at the receiver after urination(s) according to an embodiment of the present disclosure where a 10×20 array of tags are provided in the diaper. In FIG. 15C, the shadowed areas correspond to the tags that do not operate as configured or designed, while the unshadowed areas correspond to the tags that still operate as configured or designed. As mentioned above, the normal operation (i.e. as configured or designed) of a tag is considered as the indication of not contact with liquid, while the failure of a tag to operate as configured or designed might be caused by its contact with liquid. However, it is also possible for the fold in the diaper to prevent an intact tag (i.e. not in contact with liquid) from operating as configured or designed. Therefore, for determination of the liquid-containing area in a diaper, the shadowed area(s) caused by the fold shall be filtered out. As an example, this filter operation can be performed based on an image processing algorithm. In particular, since in general the liquid released in a diaper propagates or spread in the diaper to form a circle or oval area, all the shadowed areas that do not constitute a circle or oval area may be considered to be caused by fold, and thus are filtered out.

According to an embodiment of the present application, for the diaper where the tags are printed throughout a side of the liquid-impervious layer, e.g. as illustrated in FIG. 15C, the object being measured is believed to be a diaper whose saturation is to be determined, only when the signals at the receiver indicate a pre-determined number of tags functioning as configured or designed; otherwise, the measurement is considered as being performed on an object other than a diaper and thus is discarded. This is because in practice it is impossible for all the tags e.g. in the 10×20 array as illustrated in FIG. 15C to be contact with liquid, especially those outermost tags. As an example, the normal operation of the tags in the four longitudinally outermost rows (two at each end, i.e. the top two rows and the bottom two rows as illustrated in FIG. 15C) and in the two laterally outermost column (one at each end, i.e. the leftmost column and the rightmost column as illustrated in FIG. 15C) is used to indicate the object being measured is a diaper whose saturation is to be determined.

Please note that the arrangements of the tags as described above and as illustrated in the drawings are for illustrative purpose only, and the technical solutions of the present disclosure can be used with other arrangements. For example, in some embodiments of the present disclosure, instead of in an array with multiple rows and multiple columns, the tags can be arranged in a matrix that comprises two sets of intersecting groups, which can still achieve the same effect.

Some of the embodiments of the present disclosure are summarized as below.

In embodiment 1, a process for manufacturing an excretion monitoring system is provided, which comprises the steps of:
  providing, on a liquid-impervious material roll, a plurality of RF tags in an arrangement each of which is configured to respond to a signal at a different frequency;
  repeating, along the length of the liquid-impervious material roll and throughout its entire length, said step of providing the plurality of RF tags;
  cutting in a manner nondeterministic to the RF tags the liquid-impervious material roll into sections of a pre-determined length such that there contains approximately the same plurality of RF tags in each section; and
  constituting the excretion monitoring system with one of the sections;
  wherein the contact of a RF tag with the excreted fluid modifies the response by that RF tag to the signal at the corresponding frequency.

In embodiment 2, for the process according to embodiment 1, the step of cutting is performed such that in each section there contains the plurality of RF tags but not in the arrangement.

In embodiment 3, for the process according to embodiment 1, the step of cutting is performed such that in each section there contains the plurality of RF tags in the arrangement.

In embodiment 4, for the process according to any of the previous embodiments, the plurality of RF tags are arranged in sequence, and the excretion monitoring system monitors the excretion by using the sequential numbers of the RF tags, taking into account the potential discontinuity in the sequential numbers of the RF tags caused by the step of cutting in a manner nondeterministic to the RF tags the liquid-impervious material roll into sections.

In embodiment 5, for the process according to any of the previous embodiments, the excretion monitoring system monitors the excretion based on the responses from the RF tags and the respective positions of the RF tags.

In embodiment 6, for the process according to any of the previous embodiments, the step of providing the plurality of RF tags is performed by printing the plurality of RF tags on the liquid-impervious material roll.

In embodiment 7, for the process according to any of the previous embodiments, the arrangement is of the predetermined length and the arrangements provided on the liquid-impervious material roll do not overlap with each other.

In embodiment 8, a process for providing a RF tag for monitoring the excretion is provided, which comprises:
  printing, on a liquid-impervious material, a first conductive layer in which a first plate is printed and a first conductor is printed spirally with its first terminal being connected to the first plate;
  printing, over the first conductive layer, a second insulation layer in which a first insulation portion is printed over the first plate and a second insulation portion is printed from the first insulation portion towards the second terminal of the first conductor with the second terminal and at least part of the first conductor being exposed; and
  printing, over the second insulation layer, a third conductive layer in which a second plate is printed on the first insulation portion opposite to the first plate and a second conductor is printed on the second insulation portion to connect the second plate to the second terminal of the first conductor;
  wherein the RF tag is configured to respond to a signal at a frequency and the contact of any exposed part of the RF tag with the excreted fluid modifies the response by the RF tag to the signal at the frequency.

In embodiment 9, an excretion monitoring system manufactured with the process according to any of the embodiments 1-7 is provided, which comprises the plurality of RF tags each of which is configured to respond to a signal at a different frequency, wherein the excretion modifies the response by the RF tag contaminated by the excreted fluid to the signal at its respective frequency.

In embodiment 10, for the excretion monitoring system according to embodiment 9, the excretion monitoring system monitors the excretion based on the responses from the RF tags and the respective positions of the RF tags.

In embodiment 11, a method for monitoring excretion with the excretion monitoring system according to any of the embodiments 9-10 is provided, which comprises:
- transmitting, to each of the plurality of the RF tags, a signal at its respective frequency;
- determining the response by the each of the plurality of the RF tags to the signal;
- determining, from the responses of the plurality of the RF tags, whether and/or which RF tag(s) is/are contaminated by the excreted fluid.

In embodiment 12, the method according to embodiment 11 further comprises:
- determining the amount of the excreted fluid based on the contaminated RF tag(s) and its/their respective position(s).

In embodiment 13, a method is provided for detecting the excretion by using an excretion monitoring system with multiple RF tags each of which is configured to respond to a signal at a different nominal frequency, wherein the contact of a RF tag with the excreted fluid modifies the response by that RF tag to the signal at the corresponding nominal frequency, the method comprises:
- transmitting a swept frequency over a range that covers the nominal frequencies of the multiple RF tags;
- receiving the responses from the multiple RF tags, wherein the expected response from a RF tag is at its actual frequency approximating or matching to its nominal frequency; and
- determining the excretion by comparing the number of the multiple RF tags and the number of the response(s) received from the multiple RF tags at respective actual frequencies.

In embodiment 14, the method according to embodiment 13 further comprises:
- associating a response to one of the multiple RF tags based on the approximation or match between the actual frequency of the response and the nominal frequency of the one RF tag; and
- determining a RF tag as being in contact with the excreted fluid when there exist no response whose actual frequency is approximating or matching to the nominal frequency of that RF tag.

In embodiment 15, a method is provided for detecting the excretion by using an excretion monitoring system with multiple RF tags in sequence each of which is configured to respond to a signal at a different frequency, wherein the contact of a RF tag with the excreted fluid modifies the response by that RF tag to the signal at the corresponding frequency, the method comprises:
- for each of the multiple RF tags, transmitting a signal at the corresponding frequency and receiving the response from that RF tag;
- determining the failed RF tag(s) whose response(s) is/are different from the expected response(s) as configured;
- detecting the excretion based on the failed RF tag(s).

In embodiment 16, a method is provided for detecting the excretion by using an excretion monitoring system with multiple RF tags in sequence each of which is configured to respond to a signal at a different frequency, wherein the contact of a RF tag with the excreted fluid modifies the response by that RF tag to the signal at the corresponding frequency, the method comprises:
- for each of the multiple RF tags, transmitting a signal and receiving the response from that RF tag;
- determining the excretion by using the responses from the multiple RF tags and the sequential numbers of the RF tags, taking into account the potential discontinuity in the sequential numbers of the RF tags caused by the cutting in a manner nondeterministic to the RF tags during the manufacture of the excretion monitoring system.

In embodiment 17, a method is provided for detecting the excretion by using an excretion monitoring system with multiple RF tags in an array each of which is configured to respond to a signal at a different frequency, wherein the contact of a RF tag with the excreted fluid modifies the response by that RF tag to the signal at the corresponding frequency and the array comprises multiple rows and multiple columns, the method comprises:
- for each of the multiple RF tags, transmitting a signal at the corresponding frequency and receiving the response from that RF tag;
- determining the failed RF tag(s) whose response(s) is/are different from the expected response(s) as configured;
- determining some of the failed RF tag(s) as being caused by lengthwise fold(s) or bend(s) of the excretion monitoring system, by taking into account the area of all the failed RF tag(s); and
- detecting the excretion based on the rest of the failed RF tag(s).

In embodiment 18, a method is provided for detecting the excretion by using an excretion monitoring system with multiple RF tags in a matrix that comprises two sets of intersecting groups, wherein each group of RF tags in one of the two sets is configured to respond to a signal at a different frequency and the contact of a RF tag with the excreted fluid modifies the response by that RF tag to the signal at the corresponding frequency, the method comprises:
- for each group of RF tags in the one of the two sets, transmitting a signal at the corresponding frequency and receiving the response from that group of RF tags;
- determining a group of RF tags in the one of the two sets as being in contact with the excreted fluid when all RF tags in that group fail to respond to the signal at the corresponding frequency as configured.

In embodiment 19, a method is provided for detecting the excretion by using an excretion monitoring system with multiple RF tags in an array that comprises multiple rows and multiple columns, wherein each row of the RF tags is configured to respond to a signal at a different frequency and the contact of a RF tag with the excreted fluid modifies the response by that RF tag to the signal at the corresponding frequency, the method comprises:
- for each row of RF tags, transmitting a signal at the corresponding frequency and receiving the response from that row of RF tags;
- determining a row of RF tags as being in contact with the excreted fluid when all RF tags in that row fail to respond to the signal at the corresponding frequency as configured.

In embodiment 20, a system for detecting the excretion in a diaper is provided, which comprises:
- a diaper with multiple RF tags each of which is configured to respond to a signal at a different frequency, wherein the contact of a RF tag with the excreted fluid modifies the response by that RF tag to the signal at the corresponding frequency;
- a plurality of detection means each of which is configured to, for each of the multiple RF tags, transmit a signal at the corresponding frequency and receive the response from that RF tag;
- wherein during the operation, the plurality of detection means are deployed around the diaper when the diaper is worn on a diaper wearer, such that for each of the multiple RF tags in the diaper, at least one of the corresponding signal at the corresponding frequency transmitted by the plurality of detection means arrives at that RF tag and the response from that RF tag is received by at least one of the plurality of detection means; and wherein the plurality of detection means communicate with each other about the responses from the multiple RF tags, based on which the excretion is detected.

What is claimed is:

1. A process for manufacturing an excretion monitoring system, comprising steps of:
providing, on a liquid-impervious material roll, a plurality of radio frequency (RF) tags in an arrangement each of the plurality of RF tags is configured to respond to a signal at a different frequency;
repeating, along and throughout length of the liquid-impervious material roll the providing the plurality of RF tags;
cutting in a manner nondeterministic to the RF tags the liquid-impervious material roll into sections of a predetermined length such that there contains approximately the plurality of RF tags in each section; and
constituting the excretion monitoring system by using one of the sections from the liquid-impervious material roll;
wherein contact of a RF tag with an excreted fluid modifies a response by that RF tag to a signal at the corresponding frequency.

2. The process according to claim 1, wherein the cutting is performed such that in each section there contains the plurality of RF tags but not in the arrangement, or
wherein the cutting is performed such that in each section there contains the plurality of RF tags in the arrangement.

3. The process according to claim 1, wherein the plurality of RF tags are arranged in sequence, and the excretion monitoring system monitors the excretion by using sequential numbers of the RF tags, taking into account a potential discontinuity in the sequential numbers of the RF tags caused by the nondeterministic cutting of the liquid-impervious material roll into sections.

4. The process according to claim 1, wherein the excretion monitoring system monitors the excretion based on responses from the RF tags and respective positions of the RF tags.

5. The process according to claim 1, wherein the providing the plurality of RF tags is performed by printing the plurality of RF tags on the liquid-impervious material roll.

6. The process according to claim 1, wherein the arrangement includes the predetermined length and the providing the plurality of RF tags is repeated in a non overlapping manner.

* * * * *